United States Patent
Giuliani et al.

(10) Patent No.: US 12,263,195 B2
(45) Date of Patent: Apr. 1, 2025

(54) MICROBIOLOGICAL PROCESS FOR THE PRODUCTION OF BEE BREAD

(71) Applicant: GIULIANI S.P.A., Milan (IT)

(72) Inventors: Giammaria Giuliani, Montagnola (CH); Marco Gobbetti, Perugia (IT); Raffaella Di Cagno, Bari (IT); Pasquale Filannino, Barletta (IT); Vincenzo Cantatore, Ruvo di Puglia (IT); Antonio Mascolo, Milan (IT); Barbara Marzani, Carbonara al Ticino (IT)

(73) Assignee: GIULIANI S.P.A., Milan (IT)

( * ) Notice: Subject to any disclaimer, the term of this patent is extended or adjusted under 35 U.S.C. 154(b) by 573 days.

(21) Appl. No.: 17/260,731

(22) PCT Filed: Jul. 16, 2019

(86) PCT No.: PCT/IB2019/056055
§ 371 (c)(1),
(2) Date: Jan. 15, 2021

(87) PCT Pub. No.: WO2020/016770
PCT Pub. Date: Jan. 23, 2020

(65) Prior Publication Data
US 2021/0268047 A1    Sep. 2, 2021

(30) Foreign Application Priority Data
Jul. 16, 2018   (IT) .................. 102018000007229

(51) Int. Cl.
| | |
|---|---|
| *A61K 35/747* | (2015.01) |
| *A23L 21/20* | (2016.01) |
| *A23L 33/00* | (2016.01) |
| *A23L 33/135* | (2016.01) |
| *A23L 33/14* | (2016.01) |
| *A61K 8/99* | (2017.01) |
| *C12N 1/20* | (2006.01) |
| *C12R 1/225* | (2006.01) |

(52) U.S. Cl.
CPC ............ *A61K 35/747* (2013.01); *A23L 21/20* (2016.08); *A23L 33/135* (2016.08); *A23L 33/14* (2016.08); *A23L 33/40* (2016.08); *A61K 8/99* (2013.01); *C12N 1/205* (2021.05); *A23V 2002/00* (2013.01); *A23V 2400/11* (2023.08); *A61K 2800/85* (2013.01); *C12R 2001/225* (2021.05)

(58) Field of Classification Search
None
See application file for complete search history.

(56) References Cited

FOREIGN PATENT DOCUMENTS

| | | | |
|---|---|---|---|
| CN | 1488282 | A | 4/2004 |
| CN | 102389069 | A * | 3/2012 |
| CN | 104286623 | A | 1/2015 |
| CN | 105495494 | A | 4/2016 |
| CN | 106072267 | A * | 11/2016 |
| CN | 107468835 | A | 12/2017 |
| WO | 2008/136730 | A1 | 11/2008 |
| WO | 2012/102668 | A1 | 8/2012 |

OTHER PUBLICATIONS

Campos, M. G. R., Frigerio, C., Lopes, J., & Bogdanov, S. (2010). What is the future of Bee-Pollen. Journal of ApiProduct and ApiMedical Science, 2(4), 131-144. (Year: 2010).*
Daniel Tamarit, et al. Functionally Structured Genomes in Lactobacillus kunkeei Colonizing the Honey Crop and Food Products of Honeybees and Stingless Bees, Genome Biology and Evolution, vol. 7, Issue 6, Jun. 2015 pp. 1455-1473 (Year: 2015).*
Asama et at., J. App. Microbiol., 119:818-826 (2015) (Year: 2015).*
Blanco et al., World J. Microbiol. Biotechnol. 13:711-712 (1997) (Year: 1997).*
Endo et al., Systematic App. Microbiol., 36:444-448 (2013) (Year: 2013).*
Kaskoniene et al., Chem. Paper, 72:2115-2120 (2018) (Year: 2018).*
Komosinska-Vassev et al., ECAM, 297425:1-6 (2015) (Year: 2015).*
Martos et al., Biotech. Res. Int., 2013(435154):1-7 (2013), (Year: 2013).*
International Search Report and Written Opinion for corresponding Application No. PCT/IB2019/056055 (mailed Oct. 30, 2019).
Masoud et al., "Pectin Degrading Enzymes in Yeasts Involved in Fermentation of Coffea arabica in East Africa," Internat. J. Food Microbiol. 110(3):291-296 (2006).

* cited by examiner

*Primary Examiner* — Michelle F. Paguio Frising
(74) *Attorney, Agent, or Firm* — Troutman Pepper Locke LLP

(57) ABSTRACT

The present invention relates to a biotechnological process for the production of a fermented pollen comprising the inoculation of pollen with at least one lactic bacterium of the species *Lactobacillus kunkeei* and the fermentation of the pollen inoculated with the lactic bacterium. The fermented pollen obtained has nutritional and organoleptic properties similar to bee bread naturally produced inside the honeycomb of the beehive and finds application in the food and nutraceutical field.

7 Claims, 7 Drawing Sheets

MICROBIOLOGICAL PROCESS FOR THE PRODUCTION OF BEE BREAD

This application is a national stage application under 35 U.S.C. § 371 of PCT Application No. PCT/IB2019/056055, filed Jul. 16, 2019, which claims the priority benefit of Italian Patent Application No. 102018000007229, filed Jul. 16, 2018, which are hereby incorporated by reference in their entirety.

FIELD OF THE INVENTION

The present invention relates to a microbiological process for the production of bee bread.

The present invention originates in the field of biotechnological processes for the production of nutritional, dietary or food products.

In particular, the present invention relates to a biotechnological process for the production of fermented pollen similar to bee bread naturally produced in the honeycombs of the beehive.

PRIOR ART

Pollen is the male germinal element of the phanerogam plants, which is situated in powdery form in the floral anthers placed on the terminal part of the stamens of flowers and consists of microscopic structures to which the plants entrust the transport of their germ cells. The bees collect it and use it for the production of royal jelly and for feeding the larvae.

In nature, pollen is the primary source of proteins, lipids, sterols, minerals and vitamins for bees (*Apis mellifera* L.) while in the food and dietary sector it has become an object of growing interest due to its high content in nutrients.

Bees collect pollen from plant inflorescences or from the environment and deposit it in honeycombs beehive where it is mixed with nectar, honey and glandular secretions, forming granules which constitute the primary protein source for larval forms and adult insects.

The pollen inside the honeycombs of the beehive is subjected to a series of biochemical transformations mainly by lactic acid bacteria and other microorganisms. The pollen fermented inside the honeycombs is called "bee bread" (Vasquez & Olofsson, 2009).

The bee bread has a different composition with respect to the initial pollen since the latter has undergone biochemical modifications, such as the reduction of complex polysaccharides, changes in the profile of amino acids, proteins and lipids and an increase in simple carbohydrates and in the titration acidity (Lee et al., 2014; Human and Nicolson, 2006; Anđelković et al., 2012).

These variations make bee bread a microbiologically stable environment, and furthermore pollen fermentation in the honeycombs increases its digestibility and nutritional value compared to fresh pollen.

The nutritional and functional properties such as the antioxidant, anti-inflammatory, hepato-protective, anti-atherosclerosis, and immunomodulating activity make bee bread a suitable product for the human diet (Markiewicz-Żukowska et al., 2013; Nagai et al., 2004; Denisow and Denisow—Pietrzyk, 2016).

However, the quantity of available bee bread is inadequate compared to the market demand, since the removal from the honeycombs is expensive, can cause damage to the structure of the beehive and in any case the quantity present in the beehives is not able to satisfy the growing market demand. The lack of this product determines a high market price.

In an attempt to overcome these limitations and drawbacks, beekeepers collect pollen directly from foraging bees at the entrance of the beehives, with the help of "pollen traps" consisting of grids that hold pollen on their surface.

However, unlike bee bread that does not require any type of conditioning, fresh pollen is not a stable substrate and can stimulate the production of mycotoxins.

The collected fresh pollen therefore needs to be dried or frozen before being stored. However, it has been found that drying, when carried out at temperatures above 35° C., causes a loss of nutrients and volatile compounds. On the other hand, freezing has high production costs.

A compromise between the two technologies is represented by low temperature dehumidification. However, this technology has proved to be less effective than freezing in maintaining the organoleptic and nutritional properties of bee bread. Currently, therefore, it is felt the need to have bee bread of a different origin than natural, which has organoleptic and nutritional properties similar to the fresh product, in quantities adequate to meet market needs.

In view of the above, an industrial process for the production of bee bread which allows obtaining a quantity of product suitable for the needs of the market, while protecting the structure of the beehive, is part of the general objects of the present invention.

One of the objects of the present invention is to provide a microbiological process for producing bee bread with organoleptic properties similar to those of the natural product.

Another object of the invention is to provide a biotechnological process for the production of bee bread having a nutritional and functional value higher than that of fresh pollen.

SUMMARY OF THE INVENTION

The present invention originates from having observed that by carrying out a fermentation of pollen with selected fructophilic lactic bacteria, environmental conditions similar to those typical of natural fermentation that lead to the formation of bee bread are reproduced.

In particular, it has been found that by fermenting pollen with specific fructophilic lactic bacteria in combination with a selected yeast, fermented pollen is obtained which can be assimilated with naturally produced bee bread, increasing the production yield for the same starting amount of pollen.

The Applicant has therefore identified selected strains of lactic bacteria that use fructose as the preferred substrate with respect to glucose as a carbon source for the production of bee bread and used them within a biotechnological process to produce synthetically or semi-synthetically bee bread.

According to a first aspect, the present invention provides a microbiological process for the production of bee bread comprising:
- a step a) of preparation of the inoculum and inoculation of pollen with starter lactic bacteria using fructose as the preferred substrate with respect to glucose as a carbon source for the production of bee bread and
- a step b) of pollen fermentation,
- said process being characterized in that the inoculated starter lactic bacteria belong to the species *Lactobacillus kunkeei*.

The inventors have also found that the *Lactobacillus kunkeei* PF12, PF15 and PL13 strains and mixtures thereof are particularly suitable as starter lactic acid bacteria of the process of the invention.

Advantageously, the bee bread obtained with the biotechnological process of the invention is provided with a nutritional value and a longer shelf life than pollen of natural origin.

The bee bread obtained from the process of the invention also has a higher nutritional value than the pollen used as the starting material of the process. Specifically, the bee bread or fermented pollen obtained by the microbiological/biotechnological process of the invention has a total free amino acid and peptide content higher than the unfermented pollen used as starting material and a higher content of digestible proteins.

Furthermore, the bee bread or fermented pollen obtained has higher levels of soluble free phenolic compounds, typically provided with cellular antioxidant activity, than the starting pollen.

The combination of nutritional and long-lasting features of the bee bread obtained with the present process are appreciable in the nutritional and dietary context and make it suitable for the formulation of nutraceutical, dietary or food products. Advantageously, the bee bread obtained with the present process has a chemical composition typical of bee bread, obtained by protecting the structure of the hive.

According to a second aspect, the present invention provides a bee bread or fermented pollen obtained with the process defined according to any one of the embodiments described herein.

According to a third aspect of the invention, a composition is provided comprising bee bread or fermented pollen obtained with the process described herein and an edible carrier.

A further object of the present invention are selected lactic bacteria belonging to the species *Lactobacillus kunkeei* preferably selected from PF12, PF15 and PL13 and mixtures thereof.

According to one aspect, the invention relates to three bacterial strains belonging to the species *Lactobacillus kunkeei*, wherein said strains are:

*Lactobacillus kunkeei* PF12 deposited with accession number DSM 32843 on 4 Jul. 2018 at the International Deposit Center Leibniz-Institut DSMZ—Deutsche Sammlung von Mikroorganismen und Zellkulturen GmbH;

*Lactobacillus kunkeei* PF15 deposited with accession number DSM 32845 on 4 Jul. 2018 at the International Deposit Center Leibniz-Institut DSMZ—Deutsche Sammlung von Mikroorganismen und Zellkulturen GmbH;

*Lactobacillus kunkeei* PL13 deposited with accession number DSM 32844 on 4 Jul. 2018 at the International Deposit Center Leibniz-Institut DSMZ—Deutsche Sammlung von Mikroorganismen und Zellkulturen GmbH;

The three previously identified strains, whose certification is attached, were deposited to the name of the company Giuliani S.p.A, owner of the rights of the present.

BRIEF DESCRIPTION OF THE FIGURES

The features and advantages of the present invention will be evident from the accompanying drawings, wherein.

These results are indicative of the protection of the compounds tested on the induced oxidative stress and highlight the marked antioxidative effect of the fermented bee bread obtained with the process of the invention.

Figure 6A:
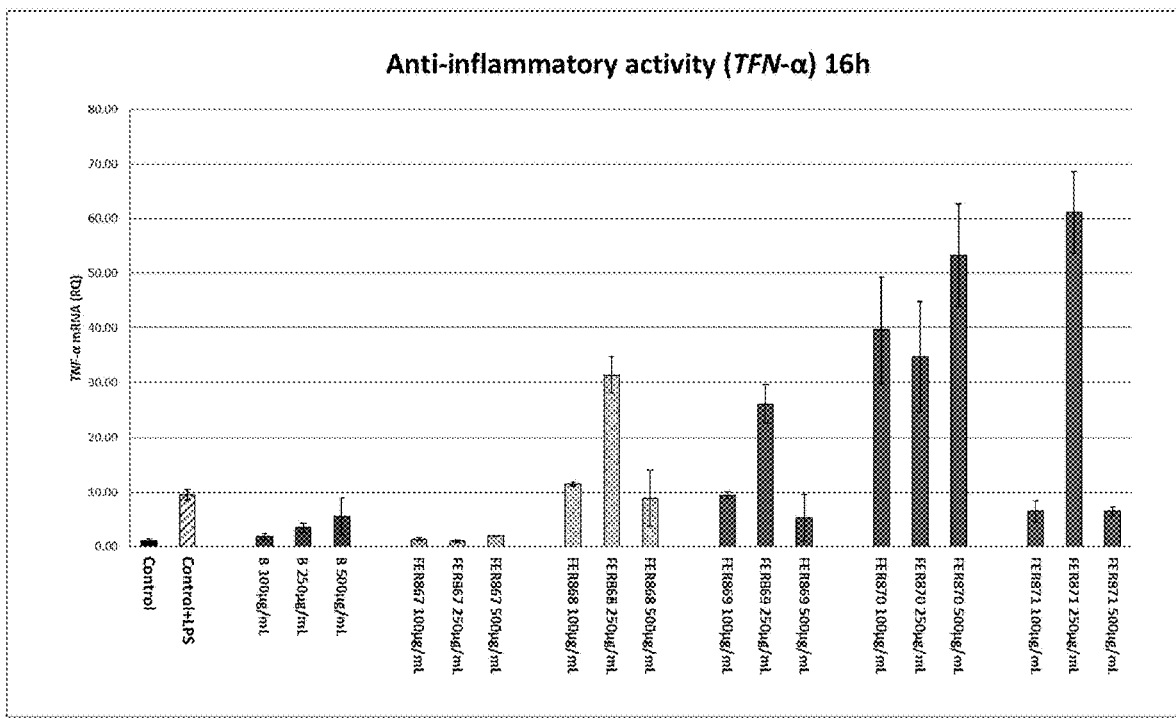
Figure 6B:
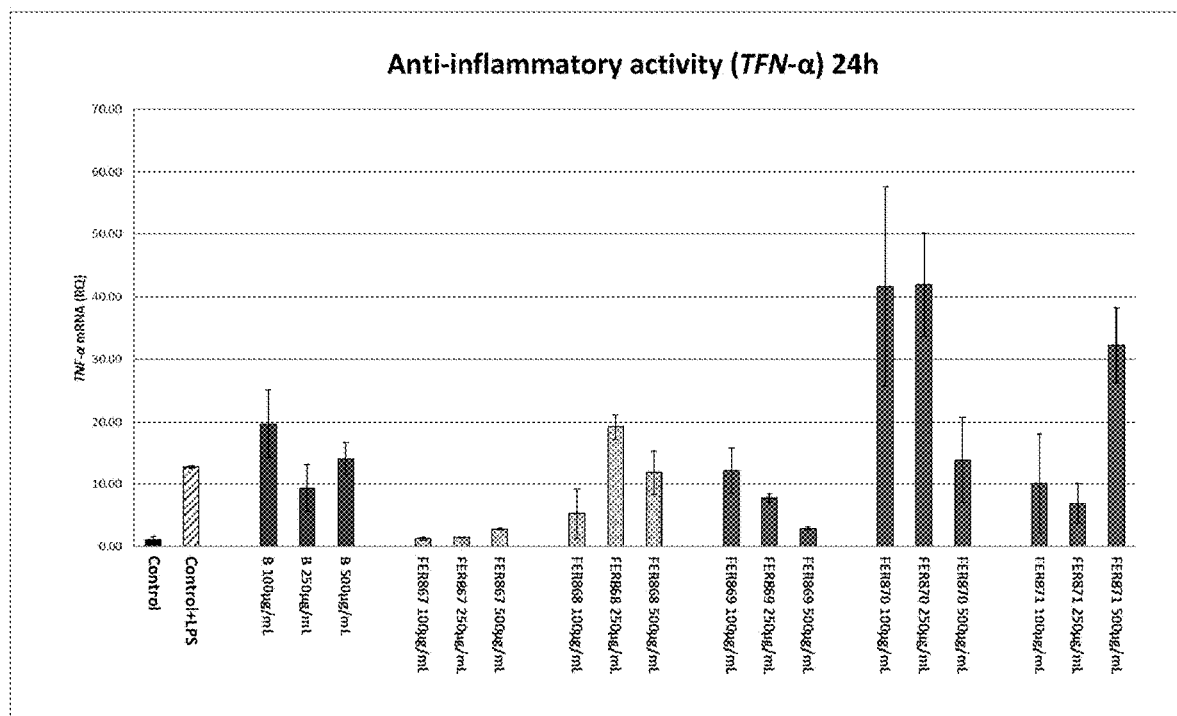

FIGS. 6A and 6B show bar graphs related to TNFα gene expression in human keratinocytes NCTC2544 evaluated by qRT-PCR according to Example 12. The cells were treated at 37° C. for 16 (A) and 24 h (B), 5% $CO_2$ with: RPMI 2.5% FCS (Control); RPMI 2.5% FCS and 10 μg/mL LPS (Control+LPS); 100, 250 and 500 μg/mL sample A (FRESH), B (CONTROL) and FER867, FER868, FER869, FER870 and FER871. Untreated cells (Control). Cells treated with 10 μg/mL of LPS (LPS). The values represent the Mean±SEM of two experiments conducted in duplicate. These results are indicative of anti-inflammatory activity and highlight the marked anti-inflammatory effect of fermented bee bread obtained with the process of the invention.

DETAILED DESCRIPTION OF THE INVENTION

According to a general aspect of the invention, a microbiological process is provided for the production of a fermented pollen similar to bee bread, in which the starting material based on pollen is inoculated with one or more selected strains of lactic bacteria advantageously of the species *Lactobacillus kunkeei*, to carry out a fermentation that substantially reproduces the fermentation that occurs in nature of the pollen stored inside the honeycombs of the hive.

According to a general aspect, the invention relates to a pollen fermentation process according to claim 1.

Further embodiments of the process of the invention are defined in claims 2-7.

The inventors have observed that the fermented pollen obtained with the process of the invention has better nutritional features, both with respect to fresh pollen and to bee bread naturally fermented in the hives together with a longer shelf life. This combination of features makes the fermented pollen obtained with the process of the invention particularly suitable as a nutritional, dietetic or nutraceutical product.

Byway of example, the total free polyphenol content present in the fermented pollen obtained with the process of the invention is equal to 84.64 g eq. gallic acid per kg dry weight, a considerably higher quantity than the content indicated in the literature for bee bread obtained with the naturally occurring fermentation which is equal to 8.9-36.52 g equivalent gallic acid per kg dry weight, as described in literature by Markiewicz-Żukowska et al., 2013; Oltica et al., 2007; Zuluaga et al., 2015.

The starting material of the process described herein is based on or consists of pollen. A suitable pollen may be fresh or dehumidified. The latter is more suitable for implementing the process on industrial scale.

A suitable dehumidified pollen is a pollen that after collection is subjected to drying in hot air flow, for example to obtain a percentage of humidity equal to or less than 12%. Low percentages of water, for example a relative humidity below 0.5 make pollen a sufficiently stable raw material if properly packaged and stored.

Typically, dehumidified pollen comes in form of granules whose colour is a function of the species or of the different botanical species visited by bees.

By way of example, a suitable dehumidified multiflora pollen has the following organoleptic features:

Appearance: small size granules, of variable colour depending on the botanical species of origin.
Odour: vegetable, of dry grass.
Taste: characteristic, vegetable, of dried flowers, of hay.
Solubility: poorly soluble in water and in organic solvents.
Water: 7 to 15%
Glucids: 25 to 48%
Proteins: 11 to 28%
Lipids: 1 to 14%
Mineral salts: 1 to 5%

Within the process described herein, the dehumidified pollen which typically occurs in form of granules or agglomerated particles, may be used as it is or it may be previously treated to degrade or break the outer shell of the granules to make the internal content available to the fermentative activity of the inoculated microorganisms.

To break the coating layer of the pollen grains, typically comprising cellulose, pectic substances, carotenoids and polyphenols, it is possible to use a physical treatment, for example a mechanical treatment or a biological treatment.

Suitable mechanical treatments include comminution, pulverization, micronization, high pressure and/or ultrasound of the pollen or a heat treatment.

To degrade the outer wall of the pollen granule it is possible to carry out a fragmentation or dimensional reduction of the granules in smaller particles or other technologies that do not substantially modify the nutritional features of the starting matrix or the pollen, or which allow obtaining products with higher nutritional value.

The degradation of the outer layer of the pollen grains may comprise a treatment for the size reduction thereof, resorting to equipment traditionally used in the food or pharmaceutical industry.

By way of example, equipment may be used which involves the passage of pollen through a metal mesh with adequate mesh gap, such as oscillating-arm granulators or the use of various types of mills such as knives, ball bearings, etc. or micronizers or combinations of these equipment.

The size reduction or comminution of the pollen grains may also be carried out using wet techniques, for example using four-way mixers with chopper and knives, stator rotor homogenizers immersed in the fluid medium, ultrasound systems and other commercially available devices.

Heat treatments may also be used optionally at higher than ambient pressure or ultrasound treatments or other processes that allow cold pasteurization with the aid of high pressures, such as High Pressure Processing (HPP).

For example, in the case of heat treatment under pressure, the pollen may be conveniently reconstituted in 10% water.

In the case of ultrasound treatment, pollen may also be used as it is.

It is also possible to use as the starting material purified pollen extracts obtained from entomophilous pollen previously subjected to one or more solvent extraction steps, for example a mixture of water and alcohol.

According to some embodiments, the outer coating layer of the pollen is broken by biological degradation, for example by treating the pollen with a yeast.

Accordingly, some embodiments of the process of the invention provide for the addition of a yeast that degrades or metabolizes the pectin component that coats the pollen grain. Typically, the addition of the yeast may take place before or during step a) of the process.

The added yeast comes into contact with the pollen grains, triggering a process of disintegration of the outer coating of the pollen which facilitates contact between the nutrients present inside the grain and the lactic bacteria inoculated in step b) of the process.

Typically, the addition of yeast is provided when the starting pollen has not been treated and in particular it has not been subjected to a mechanical action, for example of comminution or grinding, aimed at breaking the coating layer of the grain.

According to a preferred embodiment, the yeast that degrades or metabolizes the pectin component that coats the pollen grain belonging to the species *Wickerhamomyces anomalus* or *Hanseniaspora uvarum* is a mixture of the two species.

According to one embodiment, the yeast used is the *Hanseniaspora uvarum* AN8Y27B strain.

In an embodiment of the process of the invention, the inoculum is prepared using pollen itself as the growth substrate.

In other embodiments, the growth substrate of the inoculated microorganisms is a suitable culture medium such as Fructose Yeast Peptone, FYPed optionally contains yeast or vegetable extracts and peptones that provide the microorganisms with the nutrients necessary for rapid growth.

Alternatively, it is possible to use a mixture of pollen and extracts/peptones.

In a preferred embodiment of the process of the invention, the inoculum of lactic bacteria and yeast is prepared separately.

The step b) of fermentation of the process is carried out by inoculating lactic bacteria typically belonging to the genus *Lactobacillus*, conveniently of the species *Lactobacillus kunkeei*.

According to a preferred embodiment, step a) of the process comprises the inoculation of lactic bacteria belonging to the species *Lactobacillus kunkeei* selected from the *Lactobacillus kunkeei* PF12, PF15 and PL13 strains and mixtures thereof. Each of these selected bacterial strains has a capacity of growth and colony forming on a pollen-based substrate unexpectedly higher than other lactobacilli also belonging to the species *Lactobacillus kunkeei*. Furthermore, said three strains have a surprising ability to acidify and produce antimicrobial compounds, as documented in the experimental part reported in the following Examples.

Advantageously, the fermentation step of the process of the invention is carried out inside a bioreactor, typically in aerobic conditions.

According to some embodiments, the humidity of the product inside the bioreactor ranges from 30 to 95% of the total mass.

Typically, the mixture comprising the pollen and the inoculated microorganism may be in a semi-solid form when the humidity values are low, for example from 30 to 45% and in semi-solid or liquid form when the humidity values are high, for example from 60 to 95%.

According to some embodiments, the pH of the environment in the bioreactor at the beginning of step b) of fermentation is in the range of from 4 to 6.

In a preferred embodiment of the invention, the pH of the system has a value of between 5.25+/−0.25 and possibly corrected within said range by the addition of a conventional pH corrector.

Typically, during the step b) of fermentation, the following reaction parameters and conditions are monitored:
Amount of sugars (glucose and fructose)
Total titratable acidity
pH
Lactic acid and acetic acid
Cell density The process may be interrupted when the desired amounts of organic acids/cell density/free phenolic acids/residual sugars/free amino acids are obtained.

In an embodiment of the process of the invention, the obtained fermented pollen is subjected to a step c) of reducing the microbial load. According to one embodiment, the fermented pollen obtained, optionally subjected to step c), is subjected to a cold-drying step, for example it is cryo-dried, typically in a liostat. Alternatively, the fermented pollen may be stored frozen conveniently after centrifugation, at temperatures for example of the order of −40° C. or lower.

In another embodiment of the invention, the fermented pollen is lyophilized with the aim of keeping the microorganisms alive and vital. Alternatively, the fermented pollen or biomass obtained may be stored frozen, typically after centrifugation, at temperatures below 0, for example in the order of −40° C. or lower.

For the purposes of the present invention, other conventional techniques may also be used for removing water from fermented pollen, for example by resorting to spray drying.

According to one embodiment, the process of the invention comprises the following steps:
supply of starting material based on fresh non-pre-treated pollen, preferably stored at −20° C., or dried or dehumidified pollen, conveniently stored at +4° C. or at room temperature, and/or optionally pretreated by comminution, pulverization, micronization, heat treatments, high pressure, and/or ultrasound treatments, or pollen extract;

optional dilution typically with distilled water and correction of the pollen pH value until reaching the value of between 5.25+/−0.25;

inoculation of cell suspensions comprising lactic bacteria selected from the strains *L. kunkeei* PF12, PF15 and PL13 or mixtures thereof, and possibly inoculation of yeast with pectinolytic activity belonging to the genus *Wickerhamomyces*, or to the *Hanseniaspora uvarum* species, for example strain AN8Y27B;

addition of typically distilled water until a final humidity of 30 to 95% is reached. Typically, the final moisture value also includes the initial water content of the pollen for example equal to about 21.56% and the water added during the inoculation step.

Incubation at 30° C. preferably for 24-216 h in sterile tubes or in bioreactor, and isolation of the fermented pollen obtained.

According to some embodiments, the fermented pollen obtained from the process described above may be cryo-dried in a liostat or it may be frozen, preferably after centrifugation, at temperatures of about −20° C. or lower.

In certain embodiments, the fermented pollen may be subjected to treatments in order to reduce the microbial load, to remove the water or to other treatments in order to stabilize the fermented pollen.

According to a second aspect, the present invention provides a bee bread or fermented pollen obtained with the process described according to any one of the embodiments described herein. The fermented pollen obtained with the process of the invention has higher levels of free soluble phenolic compounds than the starting pollen. These and other features are illustrated in detail in the following Examples. In other embodiments of the invention, the liquid fraction possibly resulting from the step b) of fermentation is separated from the solid component and used for food, dietary or nutritional purposes.

Both liquid and solid fractions may find nutritional use.

According to a third aspect of the invention, a nutritional or dietetic composition is provided comprising the fermented pollen obtained according to any one of the embodiments described herein and an edible carrier.

According to a fourth aspect, a composition is provided comprising lactic bacteria belonging to the *Lactobacillus kunkeei* strains, *Lactobacillus kunkeei* PF12, PF15 and PL13 strains and mixtures thereof and an edible carrier.

The bacterial strains of the composition may be alive and viable or in inactivated form according to traditional techniques, for example by tyndallisation.

The compositions described herein are suitable for oral administration.

The compositions for oral administration may be in solid or liquid form. In the case of the solid form, they contain the bee bread obtained from the process described herein as a biologically active component and one or more physiologically acceptable excipients.

Typical solid form compositions comprise tablets, granules, capsules, powders, extemporaneous dosage forms, candies, chewing gums, jelly beans of different composition and shape.

The present invention applies to any solid, semi-solid and liquid dosage form which can become an edible carrier for administering the invention.

The present invention applies to all dosage forms in which the preparation is diluted before administration or used as such, being in solid, semi-solid or liquid form.

The tablets generally comprise a suitable carrier or excipient wherein the plant extract is dispersed, typically in a dry form.

In this case, suitable excipients contained in the formulation are cellulose derivatives such as hydroxymethylcellulose, hydroxypropylmethylcellulose, methylcellulose, hydroxypropylcellulose, hydroxyethylcellulose, carboxyethylcellulose, ethylhydroxyethylcellulose, cellulose acetate butyrate, cellulose acetate phthalate, and mixtures thereof.

Further examples of suitable excipients comprise polymers belonging to the lactam family such as pyrrolidone and derivatives thereof, for example polyvinylpyrrolidone, polyvinylpolypyrrolidone and mixtures thereof, inorganic salts such as calcium or dicalcium phosphate, lubricants such as magnesium stearate, triacylglycerols and mixtures thereof.

In the case of the liquid form, the composition contains the liquid fraction separated at the end of the step b) of fermentation as a biologically active component and one or more physiologically acceptable excipients.

Typical compositions in liquid form comprise solutions, emulsions, suspensions, syrups.

The bee bread or fermented pollen obtained with the process of the invention contained in the composition of the invention may be present in variable amounts, for example comprised in the range from 0.0001% to 100% by weight; from 0.001% to 50% by weight, from 0.1% by weight to 20% by weight, typically from 0.5 to 5% by weight.

According to certain embodiments, the composition of the invention further comprises one or more active substances such as vitamins, minerals, micronutrients and other active substances.

According to some embodiments, the composition for oral administration is a functional food, a nutraceutical composition, a dietary product, a complement or a nutritional product.

The composition may be marketed in conventional dosage forms such as sachet of thermo-welded aluminium of type sachet or stick pack containing a solid component or a dispersion of the solid component in a liquid, containers for the extemporaneous reconstitution of a solid in a liquid, hard or soft capsules containing a solid dispersed in a food grade oil or other compatible liquid, vials or bottles containing the dispersion of a solid in a liquid.

According to some aspects, the present invention relates to bee bread obtained according to any one of the embodiments of the process described herein or a composition which contains it for use in the treatment of metabolic, cardiovascular, bone, brain or intestine diseases or as a driver for intestinal microbiome functionality.

According to other aspects, the present invention provides the use of bee bread obtained according to any one of the embodiments of the process described herein or of a composition which contains it, for treatment by oral intake or cosmetic use of the skin in particular as anti-aging treatment or to reduce skin aging, for hair treatment.

The bee bread obtained with the process of the invention has cellular antioxidant activity and is used in preventing or treating diseases that give rise to a non-physiological production of free radicals, typically skin diseases such as tumours, precancerous or actinic diseases or redness states such as consequent to sunburns, skin blemishes, roughness or skin aging. Furthermore, the bee bread of the invention finds application in maintaining an individual's organism in physiological health conditions.

According to a further aspect, the present invention provides selected lactic bacteria belonging to the species *Lactobacillus kunkeei* selected from PF12, PF15 and PL13 and mixtures thereof.

The inventors have selected the *Lactobacillus kunkeei* PF12, PF15, and PL13 strains for surprisingly improved capacity of growth, acidification, shown in the following Table 1, for the production of antimicrobial compounds, shown in the following Tables 2 and 3, compared to other strains belonging to the same species. As an example, a protocol used for the selection of *Lactobacillus kunkeei* PF12, PF15, and PL13 bacterial strains is described below. The protocol, which is described in more detail in the following Example 1, comprises testing bacterial strains isolated from flowers, pollen, bee bread and from the gastrointestinal tract of bees.

The capacity for growth, acidification and production of antimicrobial compounds of the identified strains were tested.

An aqueous pollen extract was used as a model system for bacterial growth. The pollen extract was obtained according to the following procedure.

One hundred grams of pollen were added with glass beads, mixed with a litre of distilled water, and stirred at 500 rpm for 2 h. The mixture was centrifuged at 10,000×g for 20 minutes. The supernatant was collected, and the residue was further extracted sequentially with one litre of acidified methanol (0.1% HCl, v/v), a mixture of hexane/acetone/ethanol 50:25:25 (v/v/v), and boiling water, respectively, as described above. All the extracts were dried and dissolved in 10 ml of dimethyl sulfoxide (DMSO), mixed together and further diluted in distilled water to a final volume of 1 litre. The pollen extract was sterilized by sterile filtration on a membrane with 0.22 μm porosity. The strains were individually inoculated at a final cell density of about 7.0 log CFU/ml, and the pollen extract was incubated at 30° C. for 24 h. Growth and acidification were monitored, and the growth and acidification kinetics of the strains were mathematically modelled using the Gompertz equation. The antimicrobial activity of the strains was tested against 8 deteriorating or pathogenic indicator bacteria and 8 indicator fungi. To test the antimicrobial activity of the strains, the lactic bacteria were grown in the pollen extract at 30° C. for 24 h, and the supernatant was recovered by centrifugation at 10000×g for 10 min at 4° C. and sterilized by sterile filtration on a membrane with 0.22 μm porosity. The antibacterial activity was assayed by agar diffusion wells, while the antifungal activity was assayed by agar dilution assay.

Table 1 below shows the data of cell density, expressed as optical density, $DO_{620}$ and acidification, expressed as pH variation ($\Delta pH$) in the pollen extract fermented for 24 h at 30° C. with the lactic bacteria strains belonging to different species and isolated from flowers, pollen, bee bread and from the gastrointestinal tract of bees.

TABLE 1

| Strains | $DO_{620}$ | $\Delta pH$ |
|---|---|---|
| *Lactobacillus kunkeei* PF12 | 2.102 | 1.05 |
| *L. kunkeei* PF18 | 2.030 | 0.83 |
| *L. kunkeei* PF16 | 1.993 | 0.94 |
| *L. kunkeei* PLA21 | 1.890 | 0.71 |
| *L. kunkeei* PL13 | 1.882 | 1.03 |
| *L. kunkeei* PL9 | 1.863 | 0.66 |
| *L. kunkeei* PL28 | 1.763 | 0.97 |
| *L. kunkeei* PF15 | 1.762 | 0.69 |
| *L. kunkeei* BIII60 | 1.758 | 0.78 |

TABLE 1-continued

| Strains | DO$_{620}$ | ΔpH |
|---|---|---|
| L. kunkeei B17 | 1.758 | 0.79 |
| L. kunkeei BV61 | 1.734 | 0.95 |
| L. kunkeei PL24 | 1.682 | 0.61 |
| L. kunkeei PLA14 | 1.636 | 0.63 |
| L. kunkeei PL15 | 1.621 | 0.80 |
| L. kunkeei PFA7 | 1.601 | 0.77 |
| L. kunkeei PL33 | 1.597 | 0.81 |
| L. kunkeei PF6 | 1.551 | 0.63 |
| L. kunkeei PFA3 | 1.517 | 0.70 |
| L. kunkeei PL3 | 1.475 | 0.75 |
| L. kunkeei PLA6 | 1.473 | 0.79 |
| F. fructosus B4 | 1.426 | 0.88 |
| L. kunkeei PL31 | 1.419 | 0.62 |
| L. kunkeei PFA2 | 1.412 | 0.70 |
| L. kunkeei PLA13 | 1.402 | 0.58 |
| L. kunkeei PFB7 | 1.340 | 0.83 |
| L. kunkeei PL27 | 1.327 | 0.71 |
| Lactobacillus plantarum PLB16 | 1.228 | 0.55 |
| L. kunkeei PF7 | 1.222 | 0.69 |
| L. plantarum PLB15 | 1.123 | 0.55 |
| L. kunkeei B41 | 1.105 | 0.68 |
| L. kunkeei PLA16 | 0.921 | 0.48 |
| L. kunkeei PFA15 | 0.918 | 0.63 |
| L. kunkeei PLB30 | 0.892 | 0.59 |
| L. plantarum PLB1 | 0.822 | 0.43 |
| L. kunkeei PFA5 | 0.801 | 0.57 |
| L. kunkeei PFA35 | 0.781 | 0.42 |
| Fructobacillus fructosus MBIII5 | 0.686 | 0.22 |
| L. kunkeei B7 | 0.678 | 0.40 |
| L. kunkeei BVI14 | 0.672 | 0.28 |
| L. kunkeei PLA8 | 0.640 | 0.42 |
| L. kunkeei PFB13 | 0.581 | 0.47 |
| L. kunkeei B231 | 0.538 | 0.28 |
| L. kunkeei BVI52 | 0.426 | 0.24 |
| L. kunkeei PFA4 | 0.421 | 0.43 |
| L. kunkeei BV20 | 0.349 | 0.13 |
| F. fructosus PFB34 | 0.342 | 0.34 |
| F. fructosus PFA34 | 0.324 | 0.22 |
| L. kunkeei PFA12 | 0.308 | 0.28 |
| F. fructosus PFB29 | 0.305 | 0.27 |
| L. kunkeei PLA9 | 0.303 | 0.12 |
| F. fructosus B5 | 0.300 | 0.26 |
| L. kunkeei BIII59 | 0.296 | 0.27 |
| F. fructosus PL22 | 0.285 | 0.10 |
| F. fructosus B1 | 0.243 | 0.06 |
| F. fructosus PFA25 | 0.231 | 0.17 |
| F. fructosus PFA18 | 0.228 | 0.19 |
| L. kunkeei PFA9 | 0.224 | 0.18 |
| L. kunkeei PLB20 | 0.223 | 0.14 |
| L. kunkeei PLB18 | 0.223 | 0.14 |
| L. kunkeei PL20 | 0.182 | 0.14 |
| L. kunkeei PLB12 | 0.174 | 0.19 |
| L. kunkeei PLA24 | 0.169 | 0.13 |
| F. fructosus PFA23 | 0.135 | 0.15 |
| F. fructosus PL17 | 0.133 | 0.04 |
| L. kunkeei PFB3 | 0.123 | 0.11 |
| F. fructosus PLA1 | 0.121 | 0.09 |
| L. kunkeei PF10 | 0.112 | 0.06 |
| Lactobacillus curvatus PFB10 | 0.112 | 0.16 |
| L. kunkeei PLB17 | 0.112 | 0.12 |
| L. kunkeei PF29 | 0.110 | 0.14 |
| Lactococcus lactis PFB12 | 0.110 | 0.16 |
| L. curvatus PFB19 | 0.109 | 0.10 |
| L. kunkeei PF5 | 0.108 | 0.03 |
| F. fructosus MBIII2 | 0.108 | 0.27 |
| L. kunkeei PLB29 | 0.104 | 0.06 |
| L. kunkeei PL12 | 0.099 | 0.16 |
| F. fructosus PL10 | 0.097 | 0.11 |
| F. fructosus PLB6 | 0.096 | 0.11 |
| F. fructosus PL25 | 0.086 | 0.02 |
| L. curvatus PL34 | 0.085 | 0.10 |
| Leuconostoc citreum PFB11 | 0.084 | 0.08 |
| L. curvatus PL32 | 0.082 | 0.08 |
| F. fructosus PFB26 | 0.082 | 0.13 |
| L. curvatus PLB7 | 0.080 | 0.03 |
| L. kunkeei BVI17 | 0.080 | 0.03 |
| F. fructosus PL21 | 0.078 | 0.09 |
| L. lactis EF70 | 0.075 | 0.06 |
| L. curvatus PFB30 | 0.073 | 0.05 |
| L. curvatus PFB8 | 0.073 | 0.04 |
| L. lactis EF67 | 0.069 | 0.04 |
| L. lactis PFB15 | 0.052 | 0.04 |
| L. kunkeei PLB34 | 0.046 | 0.07 |
| L. kunkeei PF1 | 0.044 | 0.09 |

As can be seen from the experimental data, the selected *Lactobacillus kunkeei* PF12, PF15, and PL13 strains have a surprisingly higher capacity of growth, of acidification than those found for the other strains tested, belonging to the same bacterial species.

The following Table 2 shows the inhibition spectra* of the pollen extract fermented with lactic acid bacteria strains at 30° C. for 24 h. The antibacterial activity was tested against 8 strains of pathogenic or deteriorating indicator bacteria*. Unfermented pollen extract was used as a control.

TABLE 2

| | Staphylococcus aureus DSM 20231 | Listeria monocytogenes ATCC 19115 | Escherichia coli DSM 30083 | Bacillus megaterium F6 | Pantoea agglomerans DTB8 | Escherichia hermannii PS2 | Serratia marcescens DR8 | Serratia marcescens DR10 |
|---|---|---|---|---|---|---|---|---|
| Unfermented pollen extract | − | − | − | − | − | − | − | − |
| Lactobacillus kunkeei PF12 | + | +++ | +++ | ++++ | ++ | +++ | ++ | +++ |
| L. kunkeei PF16 | + | ++ | ++ | +++ | ++++ | +++ | ++ | ++ |
| L. kunkeei PL13 | + | ++ | ++ | +++++ | +++ | +++ | ++ | ++ |
| L. kunkeei PL28 | − | ++ | ++ | ++++ | ++++ | +++ | ++ | − |
| L. kunkeei BV61 | − | ++ | ++ | ++++ | ++ | − | ++ | − |
| L. kunkeei PF18 | − | + | ++ | ++++ | − | − | ++ | +++ |
| L. kunkeei B17 | + | ++ | ++ | ++++ | ++++ | + | ++ | − |
| L. kunkeei BIII60 | − | + | ++ | ++++ | + | + | ++ | − |

TABLE 2-continued

| | Staphylococcus aureus DSM 20231 | Listeria monocytogenes ATCC 19115 | Escherichia coli DSM 30083 | Bacillus megaterium F6 | Pantoea agglomerans DTB8 | Escherichia hermannii PS2 | Serratia marcescens DR8 | Serratia marcescens DR10 |
|---|---|---|---|---|---|---|---|---|
| L. kunkeei PF15 | + | ++ | +++ | +++++ | ++++ | + | +++ | +++ |
| L. kunkeei PL9 | − | + | ++ | ++++ | − | − | ++ | +++ |
| L. kunkeei PLA21 | − | + | +++ | ++++ | +++ | − | ++ | +++ |
| F. fructosus B4 | − | + | ++ | ++++ | ++ | +++ | ++ | +++ |
| L. kunkeei PFB7 | + | ++ | ++ | ++++ | +++ | +++ | ++ | − |
| L. kunkeei PL27 | − | + | + | ++++ | ++ | + | + | ++ |
| L. kunkeei PFA2 | − | ++ | ++ | +++++ | ++ | − | + | ++ |
| L. kunkeei PFA3 | − | +++ | ++ | +++ | ++++ | − | ++ | +++ |
| L. kunkeei PL3 | − | + | + | ++++ | ++ | + | + | ++ |
| L. kunkeei PLA6 | + | ++ | +++ | +++++ | + | − | ++ | +++ |
| L. kunkeei PL33 | − | + | + | +++++ | +++ | − | +++ | − |
| L. kunkeei PL15 | − | + | + | ++++ | ++ | + | + | ++ |
| L. kunkeei PFA7 | − | +++ | ++ | ++++ | +++ | − | + | ++ |
| L. kunkeei PL24 | − | + | ++ | ++++ | + | ++ | ++ | ++ |
| L. kunkeei PLA14 | + | +++ | + | +++++ | ++ | ++ | + | − |
| L. kunkeei PF6 | − | + | ++ | +++ | + | + | + | − |
| L. kunkeei PL31 | + | +++ | + | +++++ | ++ | ++ | + | − |
| L. kunkeei PLA13 | − | ++ | ++ | ++++ | ++ | ++ | ++ | − |
| Lactobacillus plantarum PLB16 | − | + | ++ | ++++ | + | + | − | − |
| L. plantarum PLB15 | − | + | ++ | +++ | + | + | − | − |
| L. kunkeei B4I | + | + | + | ++++ | + | − | + | − |
| L. kunkeei PF7 | − | ++ | +++ | ++++ | ++++ | +++ | ++ | ++ |
| L. kunkeei PFA15 | − | + | ++ | ++++ | + | + | − | − |
| L. kunkeei PLB30 | + | +++ | + | +++++ | ++ | ++ | + | − |
| L. kunkeei PFA5 | − | ++ | ++ | +++++ | ++ | ++ | ++ | ++ |
| L. kunkeei PLA16 | + | + | + | ++++ | + | − | + | − |
| L. plantarum PLB1 | − | + | + | ++++ | + | + | − | − |
| L. kunkeei PFA35 | + | +++ | +++ | +++++ | ++ | + | ++ | − |
| L. kunkeei B7 | − | ++ | ++ | +++++ | ++++ | ++ | ++ | ++ |
| L. kunkeei PLA8 | − | + | ++ | +++++ | + | ++++ | ++ | − |
| L. kunkeei PFB13 | − | ++ | ++ | +++++ | ++++ | ++ | ++ | ++ |
| L. kunkeei PFA4 | − | ++ | ++ | +++ | +++ | ++ | ++ | ++ |

*Antibacterial activity was evaluated as follows: −, no inhibition; +, inhibition halo of the diameter <1 mm; ++, inhibition halo of the diameter of 1-2.5 mm; +++, inhibition halo of the diameter 2.5-4.0 mm; ++++ inhibition halo of the diameter 4.0-6 mm; +++++ inhibition halo of the diameter >6 mm.
‡Growth conditions: Staphylococcus aureus DSM 20231, Trypticase soy yeast extract medium at 37° C.; Listeria monocytogenes ATCC 19115, Brain heart infusion medium at 37° C.; Escherichia coli DSM 30083, Luria-Bertani broth at 37° C.; Bacillus megaterium F6, Luria-Bertani broth at 30° C.; Pantoea agglomerans DTB8, Nutrient broth at 30° C.; Escherichia hermannii PS2, Nutrient broth at 30° C.; Serratia marcescens DR8, Nutrient broth at 30° C.; Serratia marcescens DR10, Nutrient broth at 30° C.

The following Table 3 shows the inhibition spectrum* of the pollen extract fermented with the lactic bacteria at 30° C. for 24 h. The antifungal activity was tested against 8 strains of indicator fungi*. The percentage of inhibition of mycelial growth was calculated with respect to the growth of the indicator strain on Potato Dextrose Agar (PDA) supplemented with unfermented pollen extract.

TABLE 3

| | Aspergillus versicolor CBS 117286 | Aspergillus niger DPPMAF3 | Penicillium roqueforti DPPMA1 | Penicillium polonicum CBS 112490 | Penicillium albocoremium CBS 109582 | Aspergillus parasiticus CBS 971.97 | Penicillium paneum CBS 101032 | Penicillium bialowiezense CBS 110102 |
|---|---|---|---|---|---|---|---|---|
| Lactobacillus kunkeei PF12 | +++ | ++ | ++ | – | ++ | – | – | – |
| L. kunkeei PF16 | +++ | – | – | – | ++ | + | – | – |
| L. kunkeei PL13 | +++ | – | – | + | ++ | ++ | ++ | – |
| L. kunkeei PL28 | – | – | – | – | – | – | – | – |
| L. kunkeei BV61 | – | – | – | – | – | – | – | – |
| L. kunkeei PF18 | – | – | – | – | – | – | – | – |
| L. kunkeei B17 | – | – | – | – | – | – | – | – |
| L. kunkeei BIII60 | – | – | – | – | ++ | – | – | – |
| L. kunkeei PF15 | – | – | – | – | – | – | – | – |
| L. kunkeei PL9 | – | – | – | – | – | – | – | – |
| L. kunkeei PLA21 | – | – | – | – | – | – | – | – |
| F. fructosus B4 | – | – | ++ | – | – | ++ | – | – |
| L. kunkeei PFB7 | – | – | – | – | – | – | – | – |
| L. kunkeei PL27 | – | – | – | – | – | – | – | – |
| L. kunkeei PFA2 | – | – | – | – | ++ | – | – | – |
| L. kunkeei PFA3 | – | – | ++ | – | – | – | – | + |
| L. kunkeei PL3 | – | – | – | – | – | – | – | – |
| L. kunkeei PLA6 | – | – | – | – | – | – | – | – |
| L. kunkeei PL33 | – | – | – | – | – | – | – | – |
| L. kunkeei PL15 | – | – | – | – | – | – | – | – |
| L. kunkeei PFA7 | – | – | – | – | – | – | – | – |
| L. kunkeei PL24 | – | – | – | – | – | – | – | – |
| L. kunkeei PLA14 | – | – | – | – | – | – | – | – |
| L. kunkeei PF6 | – | ++ | + | – | – | ++ | – | – |
| L. kunkeei PL31 | – | – | – | – | – | – | – | – |
| L. kunkeei PLA13 | +++ | – | – | – | – | – | – | – |
| Lactobacillus plantarum PLB16 | – | – | + | – | ++ | – | – | – |
| L. plantarum PLB15 | – | – | – | – | – | – | – | – |
| L. kunkeei B4I | – | – | – | – | – | – | – | – |

TABLE 3-continued

| | Aspergillus versicolor CBS 117286 | Aspergillus niger DPPMAF3 | Penicillium roqueforti DPPMA1 | Penicillium polonicum CBS 112490 | Penicillium albocoremium CBS 109582 | Aspergillus parasiticus CBS 971.97 | Penicillium paneum CBS 101032 | Penicillium bialowiezense CBS 110102 |
|---|---|---|---|---|---|---|---|---|
| L. kunkeei PF7 | – | – | – | – | – | – | – | – |
| L. kunkeei PFA15 | – | – | – | – | – | – | – | – |
| L. kunkeei PLB30 | – | – | – | – | – | – | – | – |
| L. kunkeei PFA5 | – | – | – | – | – | – | – | – |
| L. kunkeei PLA16 | – | – | – | – | – | – | – | – |
| L. plantarum PLB1 | – | – | – | – | – | – | – | – |
| L. kunkeei PFA35 | – | – | – | – | – | – | – | – |
| L. kunkeei B7 | – | – | – | – | – | – | – | – |
| L. kunkeei PLA8 | – | – | + | – | ++ | – | – | – |
| L. kunkeei PFB13 | ++ | – | + | – | – | – | – | – |
| L. kunkeei PFA4 | – | – | + | – | – | – | – | – |

*Antifungal activity was evaluated as follows: –, no inhibition; +, inhibition of radial growth of mycelium <25%; ++, inhibition of radial growth of mycelium by 25-50%; +++, inhibition of radial growth of mycelium by 50-75%; ++++ inhibition of radial growth of mycelium >75%.
‡Growth conditions: Potato Dextrose Agar at 25° C. for 8 days.

The experimental data of Tables 2 and 3 further highlight that the selected *Lactobacillus kunkeei* PF12, PF15, and PL13 strains have a surprisingly higher antimicrobial activity than that found for the other strains tested, belonging to the same or other bacterial species.

Terminology

In the present context, the term pollen means entomophilous pollen collected by foraging bees and processed by them; said pollen may come from a single botanical species (monoflora) or from several botanical species (multiflora).

Functional food means any modified food or food ingredient that can provide a benefit or protection against a problem or a physiological condition, in addition to the traditional nutrients that are contained in it.

Nutraceutical product means a product isolated or purified from edible substances. A nutraceutical is such when it is shown that it has a physiological benefit or that it provides protection against a problem or physiological disorder.

Dietary or food supplement means a product that contains a vitamin, mineral, plant extract, amino acid, metabolite, extract, concentrate or mixtures of these ingredients.

The term edible carrier means any edible carrier that can be used in the formulation of a food, nutraceutical or dietary/food supplement.

Within the scope of the present description, the terms bee bread and fermented pollen obtained with the process of the invention designate the same product and are interchangeable.

The organoleptic and/or nutritional properties of traditional bee bread described in the previous chapter dedicated to the prior art are substantially similar to those of fermented pollen obtained with the process of the invention.

The following examples are provided for illustrative purposes only of some embodiments of the invention.

Example 1

Protocol for the Selection of Bacterial Strains of *Lactobacillus kunkeei* PF12, PF15 and PL13

In order to select the three strains of lactic starter bacteria, 93 strains belonging to different species and isolated from flowers, pollen, bee bread and the gastrointestinal tract of bees were tested for their ability to grow, acidify and produce antimicrobial compounds.

Pollen extract was used as a model system for bacterial growth. The pollen extract was obtained as follows.

One hundred grams of pollen were added with glass beads, mixed with a litre of distilled water, and stirred at 500 rpm for 2 h. The mixture was centrifuged at 10000×g for 20 minutes. The supernatant was collected, and the residue was further extracted sequentially with one litre of acidified methanol (0.1% HCl, v/v), a mixture of hexane/acetone/ethanol 50:25:25 (v/v/v), and boiling water, respectively, as described above. All the extracts were dried and dissolved in 10 ml of dimethyl sulfoxide (DMSO), mixed together and further diluted in distilled water to a final volume of 1 litre. The pollen extract was sterilized by sterile filtration on a membrane with 0.22 μm porosity. The strains were individually inoculated at a final cell density of about 7.0 log CFU/ml, and the pollen extract was incubated at 30° C. for 24 h. Growth and acidification were monitored, and the growth and acidification kinetics of the strains were mathematically modelled using the Gompertz equation. The antimicrobial activity of the strains was tested against 8 deteriorating or pathogenic indicator bacteria and 8 indicator fungi. To test the antimicrobial activity of the strains, the lactic bacteria were grown in pollen extract at 30° C. for 24 h, and the supernatant was recovered by centrifugation at 10000×g for 10 min at 4° C. and sterilized by sterile filtration on a membrane with 0.22 μm porosity. The antibacterial activity was assayed by agar diffusion wells, while the antifungal activity was assayed by agar dilution assay.

The *L. kunkeei* PF12, PF15, and PL13 strains were selected because they had better capacity of growth, acidification (Table 1 above) and production of antimicrobial compounds (Tables 2 and 3 above).

Example 2

Fermentation of Pollen Extract Using Lactic Bacteria

The pollen extract, obtained according to the protocol described in Example 1, was used as a model system for the growth of 93 lactic bacteria, in order to test the capacity thereof for growth and acidification. The strains were grown in FYP broth (10 g D-fructose, 10 g yeast extract, 5 g polypeptone*, 2 g sodium acetate, 0.5 g Tween 80, 0.2 g $MgSO_4 \cdot 7H_2O$, 0.01 g $MnSO_4 \cdot 4H_2O$, 0.01 g $FeSO_4 \cdot 7H_2O$, 0.01 g NaCl per litre of distilled water [pH 6.8]) at 30° C. for 24 h. The cells were recovered by centrifugation (10000×g for 10 min at 4° C.), washed twice in 50 mM phosphate buffer pH 7.0, and suspended in the pollen extract to a final density of about 7 Log CFU/ml. The pollen extract was then incubated at 30° C. for 24 h. Growth (optical density, $DO_{620}$) and acidification (pH change, $\Delta pH$) were monitored during incubation.

Results

Ninety-three lactic acid bacteria strains belonging to different species were tested for their capacity of growth and acidification in the pollen extract (Table 1). The highest values of cell density ($DO_{620}$ 1.473-2.102) and the highest acidification capacity were found in pollen extracts fermented with strains belonging to the species *Lactobacillus kunkeei* (Table 1).

Example 3

Antimicrobial Activity of Pollen Extract Fermented with the Selected Lactic Acid Bacteria Strains.

To test the ability of lactic acid bacteria to produce antimicrobial compounds during pollen fermentation, the bacteria were grown in pollen extract, as described in Example 1, and the supernatant was recovered by centrifugation (10000×g for 10 min at 4° C.) and sterilized by sterile filtration on a membrane with 0.22 μm porosity. The antibacterial activity of the extract was assayed by diffusion assay from agar wells. The analyses were conducted on a double layer consisting of 15 ml of agar-water (2% agar, w/v) and 5 ml of the specific agar medium for growth of the indicator strain (Table 2), and inoculated to a cell density of about 4 Log CFU/ml with the cells recovered from a culture of the indicator strain incubated for 24 h at the optimal growth temperature. The wells (5 mm in diameter) were made in the double layer, and 100 μl of the fermented and cell-free pollen extract were added to each well. Unfermented pollen extract was used as a control. The plates were stored for 1 h at 4° C. to allow the radial diffusion of the pollen extract, and incubated at 30 or 37° C. for 24 h. The antifungal activity of the extract was assayed by agar dilution assay, evaluating the radial growth rate of the fungal mycelium used as an indicator (Table 3). The fermented and cell-free pollen extract was added at a concentration of 30% (v/v) to the growth medium (Potato Dextrose Agar, PDA), and 15 ml of the medium were poured into Petri dishes (90 mm diameter). The control plates contained only PDAs, without the addition of pollen extract. The assay was conducted by placing 3 mm diameter mycelium caps in the centre of the Petri dishes containing the culture medium. The radial growth of the mycelium (diameter in mm) was determined after 8 days of incubation at 25° C. in aerobic conditions. The growth inhibition percentage is calculated as follows: [(growth of the mycelium in the control−growth of the mycelium in the presence of the pollen extract)/growth of the mycelium in the control]×100. The results are expressed as the average of at least 4 measurements of mycelial growth.

Results

The fermented pollen extracts had a high antibacterial and antifungal activity, significantly ($P<0.05$) higher than the unfermented pollen extract (Tables 2 and 3). The use of the *L. kunkeei* PF12, PF15 and PL13 strains in the form of mixed starters ensures the widest inhibition spectrum.

Example 4

Protocol for the preparation and inoculation of cultures of *Lactobacillus kunkeei* PF12, PF15, and PL13
1) Growing the *L. kunkeei* PF12, PF15 and PL13 strains in FYP broth (10 g D-fructose, 10 g yeast extract, 5 g polypeptone*, 2 g sodium acetate, 0.5 g Tween 80, 0.2 g $MgSO_4 \cdot 7H_2O$, 0.01 g $MnSO_4 \cdot 4H_2O$, 0.01 g $FeSO_4 \cdot 7H_2O$, 0.01 g NaCl per litre of distilled water [pH 6.8]) at 30° C. for 24 h.
2) Centrifuging each culture broth at 10000×g for 10 min at 4° C.
3) Removing the supernatant and resuspending the cells in physiological solution (9 g/l of NaCl).
4) Centrifuging each cell suspension at 10000×g for 10 min at 4° C.
5) Remove the supernatant and resuspending the cells in physiological solution (9 g/l of NaCl).
6) Centrifuging each cell suspension at 10000×g for 10 min at 4° C.
7) Removing the supernatant and resuspend the cells in physiological solution (9 g/l of NaCl).
8) Bringing each cell suspension to a cell density of 9 Log CFU/ml corresponding to an optical density of 0.25 read on the spectrophotometer at a wavelength of 620 nm on a cuvette containing 100 μl of cell suspension and 900 μl of water.
9) Adding the cell suspensions of each strain to the pollen (previously thawed and brought to room temperature) according to a ratio of 1:10 in order to obtain a final inoculum corresponding to 8 Log CFU/g.

*Polypeptone may be replaced with other protein hydrolysates (e.g. peptone, meat extract, tryptone).

Example 5

Protocol for the preparation and inoculation of the culture of *Wickerhamomyces anomalus* or *Hanseniaspora uvarum* AN8Y27B or other yeast belonging to the *Wickerhamomyces* or *Hanseniaspora* genera:
1) Growing *Wickerhamomyces anomalus* or *Hanseniaspora uvarum* AN8Y27B, or another yeast belonging to the *Wickerhamomyces* or *Hanseniaspora* genera in Yeast Extract Peptone Dextrose broth (YPD, Oxoid) at 30° C. for 48-72 h.
2) Centrifuging the culture broth at 10000×g for 10 min at 4° C.
3) Removing the supernatant and resuspending the cells in physiological solution (9 g/l of NaCl).
4) Centrifuging the cell suspension at 10,000×g for 10 min at 4° C. 5) Removing the supernatant and resuspending the cells in physiological solution (9 g/l of NaCl).

6) Centrifuging the cell suspension at 10000×g for 10 min at 4° C.
7) Removing the supernatant and resuspending the cells in physiological solution (9 g/l of NaCl).
8) Bringing the cell suspension to a cell density of 7 Log CFU/ml corresponding to an optical density of 0.1 read on the spectrophotometer at a wavelength of 600 nm on a cuvette containing 100 μl of cell suspension and 900 μl of water.
9) Centrifuging the cell suspension at 10000×g for 10 min at 4° C., removing the supernatant, and resuspend the cells in a volume 100 times lower than the initial volume
10) Adding the cell suspension of the strain to the pollen (previously thawed and brought to room temperature) according to a ratio of 1:10 in order to obtain a final inoculum corresponding to 8 Log CFU/g.

Example 6

Protocol for the Preparation and Inoculation of Cultures of *Lactobacillus kunkeei* PF12, PF15, and PL13
  1) Growing *L. kunkeei* PF12, PF15 and PL13 in FYP broth (10 g D-fructose, 10 g yeast extract, 5 g polypeptone*, 2 g sodium acetate, 0.5 g Tween 80, 0.2 g $MgSO_4.7H_2O$, 0.01 g $MnSO_4.4H_2O$, 0.01 g $FeSO_4.7H_2O$, 0.01 g NaCl per litre of distilled water [pH 6.8]) at 30° C. for 24 h for the preparation of the pre-inoculum.
  2) Transferring the culture of the pre-inoculum of each strain by 10% in the growth medium prepared with the dried pollen in granules and stored at +4° C., pretreated with a mill or granulator in order to at least partially break the outer coating layer of the granules, resuspended in sterile demineralized water at a concentration of between 10 and 20% (weight/weight) and brought to a pH value of between 5.25+/−0.25; incubating at 30° C. for 24 h
  3) Inoculating the cultures of each strain in a bioreactor according to a 1:10 ratio so as to obtain a final inoculum corresponding to 7-8 Log CFU/g. The growth medium is prepared with the pollen dried in granules and stored at +4° C., pretreated in order to weaken the outer wall of the granules, as described in point 1, resuspended in sterile demineralized water to a concentration of between 10 and 20%.
    *Polypeptone may be replaced with other protein hydrolysates (e.g. bacteriological peptone, meat extract, tryptone).

Example 7

Fermentation of Fresh Pollen Using the Mixed Starter Composed of the Selected Strains *Lactobacillus kunkeei* PF12, PF15 and PL13 and of the Yeast *Hanseniaspora uvarum* AN8Y27B.
  1) Raw material: fresh pollen not pre-treated and stored at −20° C.
  2) Inoculum of the mixed starter composed of *L. kunkeei* PF12, PF15 and PL13, and *H. uvarum* AN8Y27B inoculated at a cell density of $10^8$ CFU/g. The protocols for the preparation and inoculation of the cultures of *L. kunkeei* PF12, PF15, and PL13, and of *H. uvarum* AN8Y27B are described in examples 4 and 5.
  3) Adding distilled water until having a final humidity of 40% (the final moisture value must also include the initial water content of the pollen [about 21.56%] and the water added during the inoculation step).
  4) Incubating at 30° C. for 216 h in 50 ml sterile tubes.

Results

Figure 1:
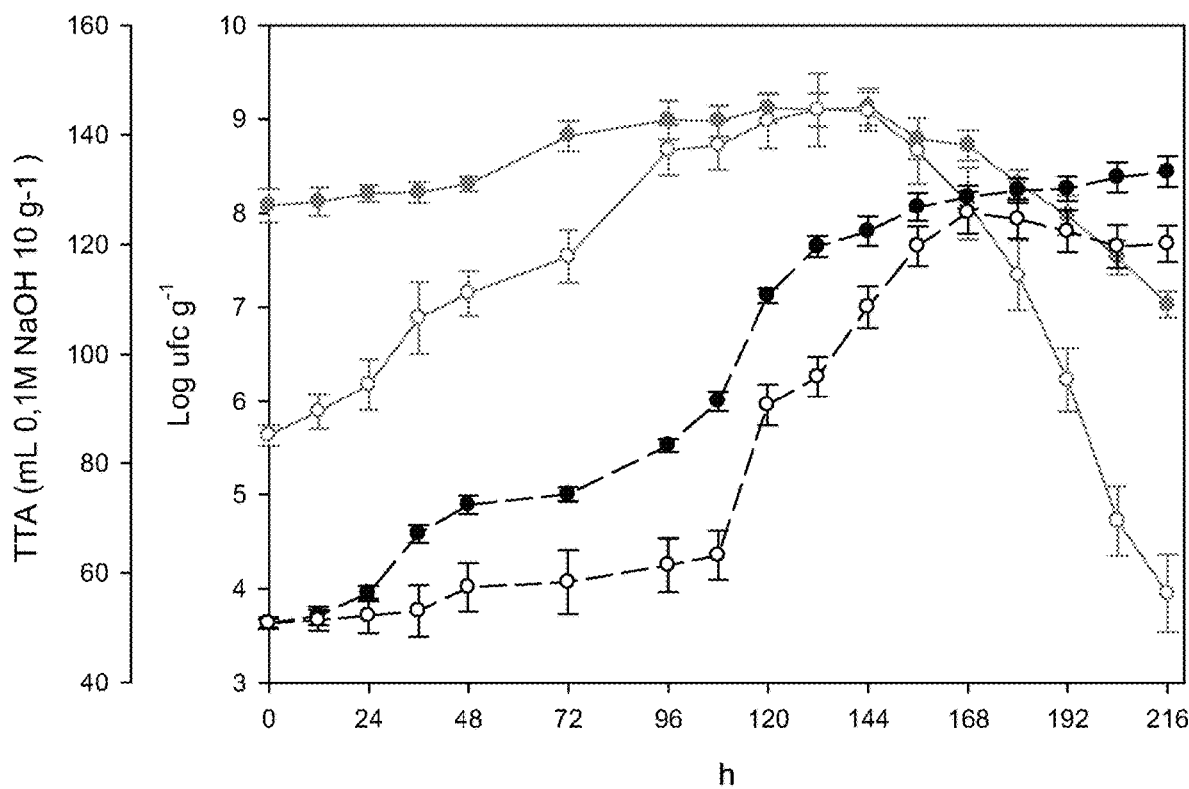
FIG. 1 shows a graph showing the cell density values of lactic bacteria (Log CFU $g^{-1}$) (solid lines) and titratable acidity (mL 0.1M NaOH 10 $g^{-1}$) (TTA) (dashed lines) during the incubation at 30° C. for 9 days of the pollen inoculated with the mixed starter (composed of *Lactobacillus kunkeei* PF12, PL13 and PF15 and *Hanseniaspora uvarum* AN8Y27B) (solid symbols) and non-inoculated pollen subjected to spontaneous fermentation (blank symbols)

A fermentation protocol of fresh pollen was defined, which involves inoculation to a density of 8 Log CFU/g of a mixed starter composed of the selected strains of *Lactobacillus kunkeei* PF12, PL13 and PF15, and *Hanseniaspora uvarum* AN8Y27B, and incubation at 30° C. for 216 h with a final pollen humidity of 40%. The growth of lactic bacteria and the acidification during incubation were monitored during fermentation by plate counting on FYP agar and determination of titratable acidity (TTA) (FIG. 1). The cell density of the TTA lactic bacteria was monitored during the spontaneous fermentation of the non-inoculated pollen (control), treated in the same conditions except for the mixed starter inoculation (FIG. 1). With the addition of the selected mixed starter, the cell density of the lactic acid bacteria in the pollen reached about 9 Log CFU $g^{-1}$ after 96 h, and remained constant up to 144 h, and decreased to about 7 Log CFU $g^{-1}$ during the remaining incubation time. Otherwise, during the spontaneous fermentation of the pollen, the lactic bacteria reached the density of about 9 Log CFU $g^{-1}$ only after 120 h, and rapidly fell to 4 Log CFU $g^{-1}$ during the remaining incubation time. The increase in TTA during fermentation was consistent with the growth of lactic bacteria. During the spontaneous fermentation of the pollen, the acidification was slower and less intense (P<0.05) compared to the fermentation conducted with the selected mixed starter.

Example 8

Pollen Fermentation Protocol
  1) Raw material: fresh pollen not pre-treated and stored at −20° C., or dried or dehumidified pollen stored at +4° C. or at room temperature, and pretreated by pulverizing and correcting the pH value of the pollen until reaching a value of between 5.25+/−0.25,
  2) Inoculation, at a cell density of 107 CFU/g, of mixed starter composed of the selected lactic bacteria *L. kunkeei* PF12, PF15 and PL13, and of the yeast *Wickerhamomyces anomalus*,
  3) Addition of distilled water to a final humidity of 70%,
  4) Incubation at 30° C. for 60 h in sterile tubes or bioreactor.
  Fermented pollen is cryo-dried in a liostat.

Example 9

Pollen Fermentation Protocol in Bioreactor Using the Selected *Lactobacillus kunkeei* PF12, PF15 and PL13 Strains without the Yeast Inoculation with Mechanical Pretreatment
  1) Raw material: pollen dried in granules and stored at +4° C., mechanically pretreated in a mill or granulator, in order to break the outer wall of the granules resuspended in the bioreactor in sterile demineralized water to a concentration of between 10 and 20% (weight/weight) leading to a final volume of 5 L
  2) Correction of the pH value until reaching the value of between 5.25+/−0.25.
  3) Inoculation of the starter composed of *L. kunkeei* PF12, PF15 and PL13 at a cell density of between 107 and $10^8$ CFU/g. The protocol for the preparation and inoculation of the cultures of *L. kunkeei* PF12, PF15 and PL13 is described in the following Example 6.

4) Incubating at 30° C. for 2-4 days while stirring at 70-100 rpm to keep the fermentation medium homogeneous.
5) The fermented pollen is cryo-dried in a liostat (9A) or dried by spray drying (9B).

Example 10

Pollen Fermentation Protocol in Bioreactor Using the Selected *Lactobacillus kunkeei* PF12, PF15 and PL13 Strains without the Yeast Inoculation with Thermal Pretreatment 1) Raw material: dehumidified pollen in granules, thermally pretreated (121° C. for 15') resuspended in the bioreactor in sterile demineralized water at a concentration of between 10 and 20% (weight/weight) leading to a final volume of 5 L
2) Correction of the pH value until reaching the value of between 5.25+/−0.25.
3) Inoculation of the starter composed of *L. kunkeei* PF12, PF15 and PL13 at a cell density of between $10^7$ and $10^8$ CFU/g. The protocol for the preparation and inoculation of the cultures of *L. kunkeei* PF12, PF15 and PL13 is described in the following Example 6.
4) Incubating at 30° C. for 2-4 days while stirring at 70-100 rpm to keep the fermentation medium homogeneous.
5) The fermented pollen is cryo-dried in a liostat (10A) or dried by spray drying (10B).

Example 11

Nutritional Enhancement of the Fermented Pollen Using the Mixed Starter Composed of the Selected Strains *Lactobacillus kunkeei* PF12, PF15 and PL13 and of the Yeast *Hanseniaspora uvarum* AN8Y27B.

Figure 2:
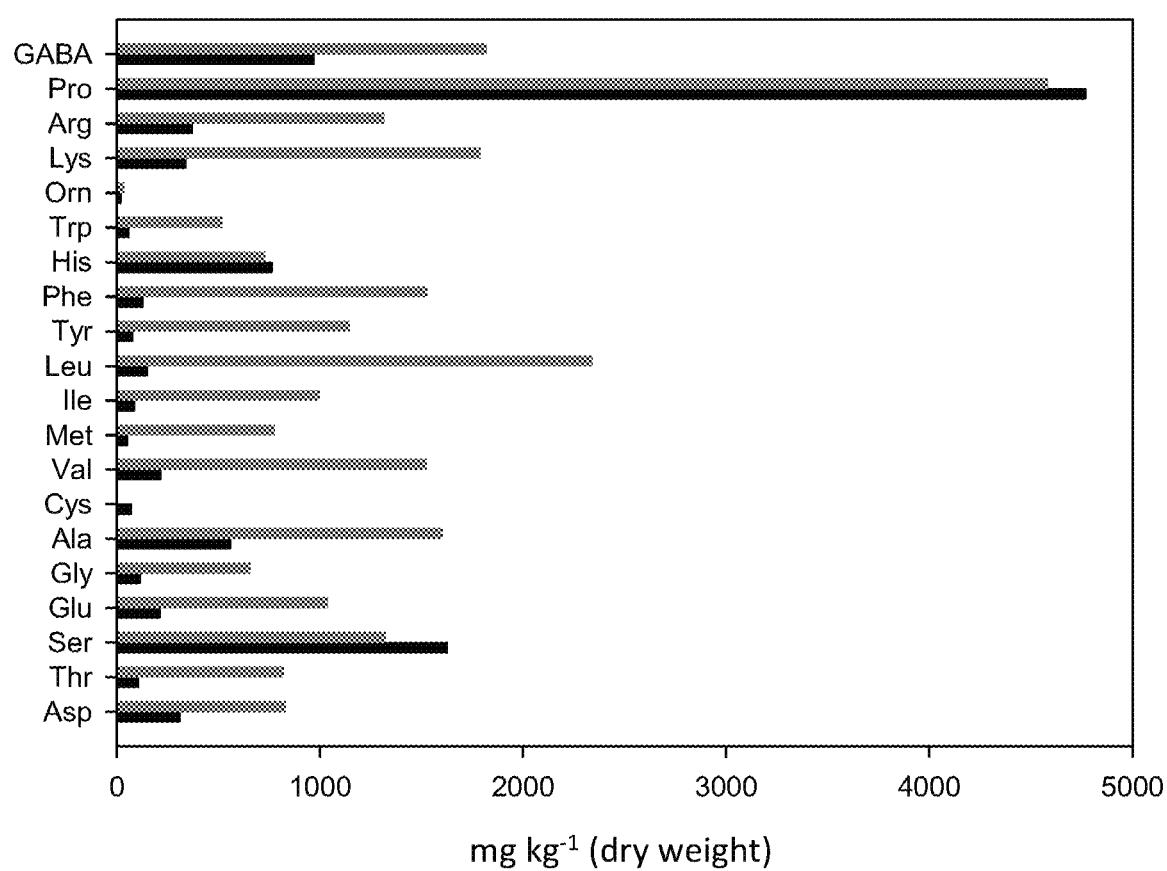
FIG. 2 shows the concentration values (mg $kg^{-1}$) of free amino acids in fresh pollen (black bars) and in pollen fermented at 30° C. for 216 h (red bars) with the mixed starter (composed of *Lactobacillus kunkeei* PF12, PL13 and PF15 and *Hanseniaspora uvarum* AN8Y27B)
Figure 3:
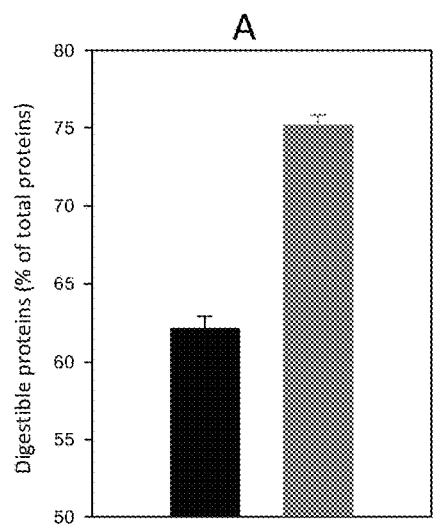
FIG. 3 shows a bar chart A with the in vitro digestibility values of proteins (expressed as % of total proteins) in fresh pollen (black bar) and in pollen fermented at 30° C. for 216 h (red bar) with the mixed starter (composed of *Lactobacillus kunkeei* PF12, PL13 and PF15 and *Hanseniaspora uvarum* AN8Y27B), and a graph B showing two curves relating to the peptide profile determined by molecular exclusion chromatography (RP-FPLC, 214 nm) in fresh pollen (black bar) and in the pollen fermented at 30° C. for 216 h (red bar) with the mixed starter (composed of *Lactobacillus kunkeei* PF12, PL13 and PF15 and *Hanseniaspora uvarum* AN8Y27B)
Figure 3:
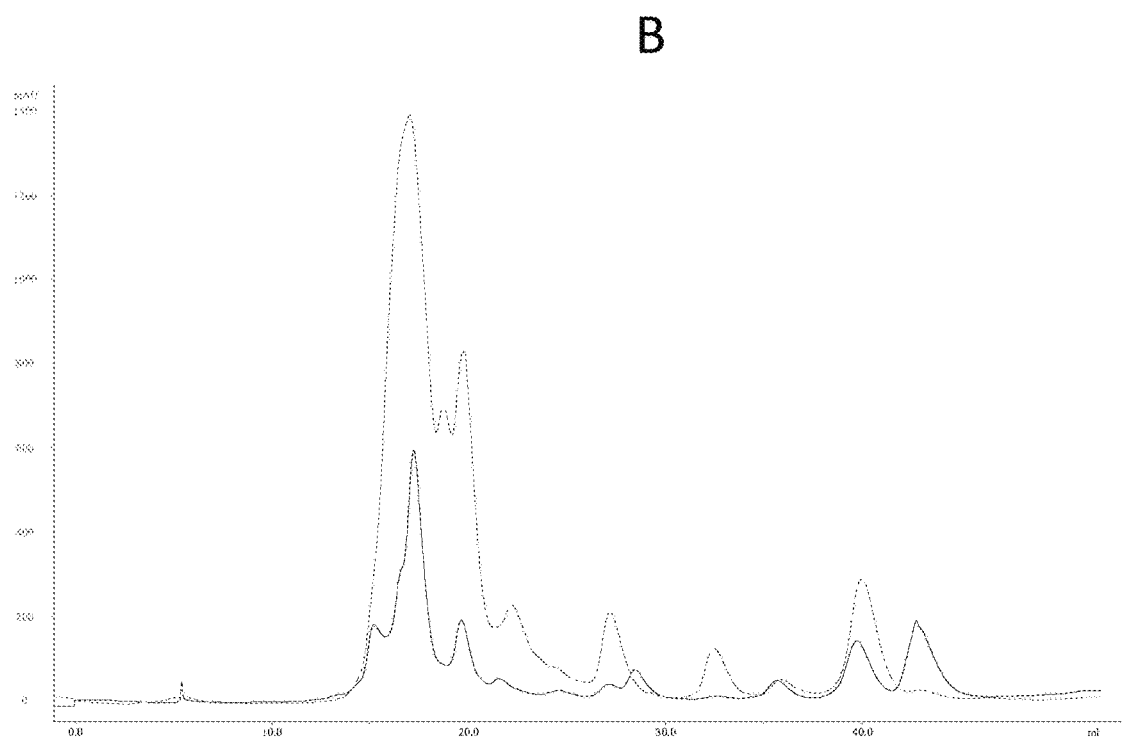
Figure 4:
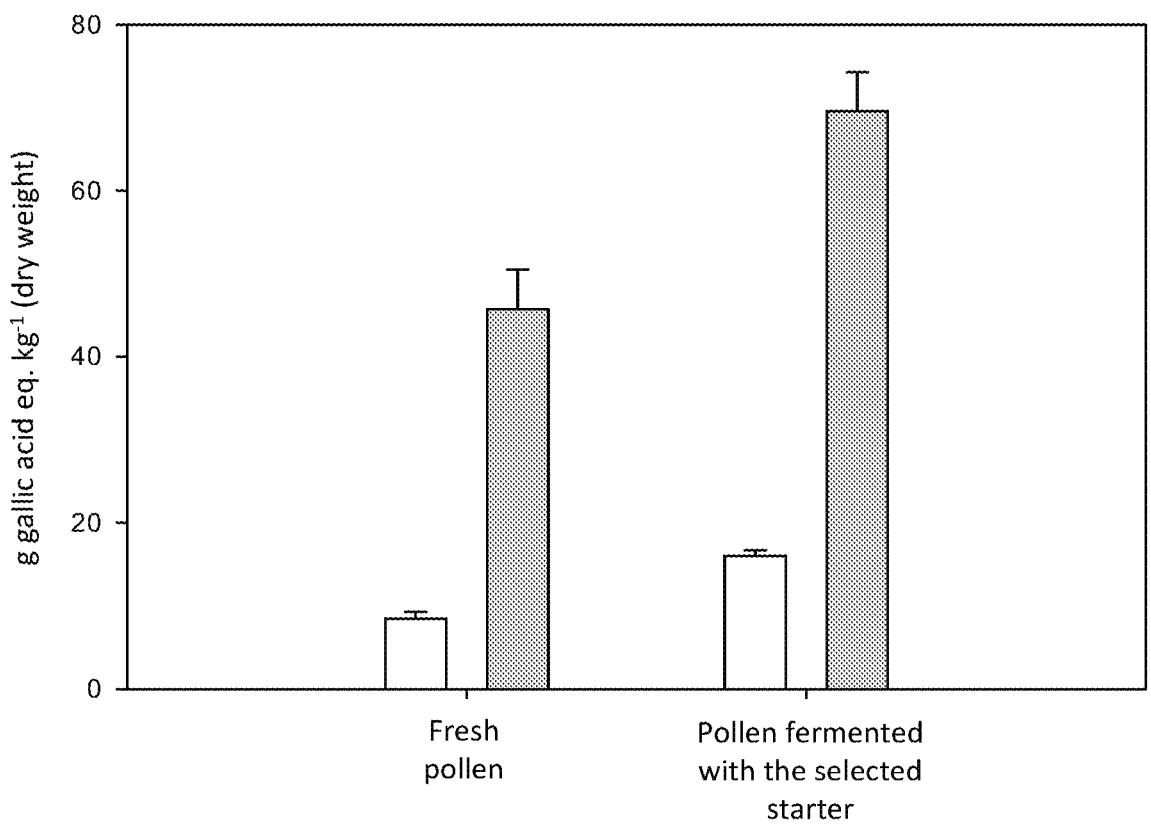
FIG. 4 shows bar graphs related to the concentration (g gallic acid eq $kg^{-1}$ dry weight) of the water-soluble free phenolic compounds (white bars) and methanol (grey bars) in fresh pollen and in pollen fermented at 30° C. for 216 h with the mixed starter (composed of *Lactobacillus kunkeei* PF12, PL13 and PF15 and *Hanseniaspora uvarum* AN8Y27B).

The fermented pollen obtained according to the protocol described in Example 7 was characterized from a chemical and nutritional point of view. The single, total and free amino acid content in the pollen was determined by the Biochrom 30 Amino Acid Analyzer (Biochrom Ltd., Cambridge Science Park, England) equipped with a cation exchange column (FIG. 2). A multi-phase protocol, which simulates in vitro digestion, was used to estimate the digestibility of pollen proteins (FIG. 3). Furthermore, the peptide profile of the pollen was analysed using the AKTA FPLC system equipped with a Superose 12 10/300 GL column and a 214 nm UV detector (FIG. 3). The content in free phenolic compounds, soluble in water and methanol, was determined by the Folin-Ciocalteu assay (FIG. 4).

Results

A significant increase (P<0.05) in total free amino acids was observed in the fermented pollen using the mixed starter composed of *Lactobacillus kunkeei* PF12, PL13 and PF15 and *Hanseniaspora uvarum* AN8Y27B (FIG. 2) and peptides (FIG. 3) of about 14 and 12 g $kg^{-1}$ (dry weight), respectively, compared to fresh pollen. Furthermore, the fermented pollen showed a greater (P<0.05) content in digestible proteins (75.14±0.7%) compared to the fresh pollen (62.11±0.8%) (FIG. 3). Furthermore, higher levels (P<0.05) of water-soluble (15.98±0.64 g gallic acid eq. $kg^{-1}$ dry weight) and methanol-soluble (69.53±4.52 g gallic acid eq. $kg^{-1}$ dry weight) free phenolic compounds were found in the fermented pollen compared to fresh pollen (8.43±0.85 and 45.73±4.81 g gallic acid eq. $kg^{-1}$ dry weight).

Example 12

1. Experimental Tests

2. Purpose of the Experimental Work

The experimental procedure reported below aims to study the in vitro activity of different tests of fermented pollen (Bee Bread) in order to characterize the antioxidant activity and anti-inflammatory activity (TNF-α) thereof on the line of human keratinocytes.

3. Materials

| | | 3.1 Tested samples | | | | |
|---|---|---|---|---|---|---|
| INTERNAL NAME | B | FER 867 | FER 868 | FER869 | FER 870 | FER871 |
| UNIQUE IDENTIFICATION NAME | CONTROL | FERMENTED | FERMENTED | FERMENTED | FERMENTED | FERMENTED |
| LOT | Lot 06/03/18B | | | | | |
| DESCRIPTION | Pollen incubated at 30° C. for 9 days without inoculation | Strains inoculated *L. kunkeii* PF12, *L kunkeii* PF15 *L. kunkeii* PL13. 121° C. for 5' | Strains inoculated *L. kunkeii* PF12, *L kunkeii* PF15 *L. kunkeii* PL13 121° C. for 5' | Strains inoculated *L. kunkeii* PF12, *L kunkeii* PF15 *L. kunkeii* PL13 | Strains inoculated *L. kunkeii* PF12, *L. kunkeii* PF15 *L. kunkeii* PL13 *H. uvarum* AN8Y27B | Strains inoculated *L. kunkeii* PF12, *L kunkeii* PF15 *L. kunkeii* PL13 121° C. for 5' |
| STORAGE | 4° C. | 4° C. | 4° C. | 4° C. | 4° C. | 4° C. |
| CONCENTRATIONS | 100-250-500-µg/mL | 100-250-500-µg/mL | 100-250-500-µg/mL | 100-250-500-µg/mL | 100-250-500-µg/mL | 100-250-500-µg/mL |

* The selected starter is composed of *L. kunkeei* PF12, PF15, and PF3, and *Wickerhamomyces anomalus* LCF1695

The fermented products were kept at 30° C. for 12 hours.

All extracts were diluted 50 mg/ml in culture medium (100% solution-solubility stock) and sterile-filtered (5 mg/mL). The stocks were stored at −20° C.

3.2 Reagents and instrumentation used

| REAGENTS | SUPPLIER |
| --- | --- |
| 30% hydrogen peroxide | SIGMA, 216763 |
| Agarose (For routine use) | SIGMA, A9539-100G |
| RPMI-1640 MEDIUM | SIGMA, R0883 |
| FETAL BOVINE SERUM | SIGMA, F7524 |
| Dimethylsulfoxide | SIGMA, D2438-50ML |
| Gentamicin solution | SIGMA, G1272 |
| L-glutamine | SIGMA, G7513 |
| Dulbecco's Phosphate Buffered Saline | SIGMA, D8537 |
| Ethidium bromide solution (10 mg/mL, for molecular biology, aqueous solution) | SIGMA, E1510 |
| Gel Loading Buffer | SIGMA, G2526 |
| RNAse, none detected | |
| MTT | SIGMA-Aldrich, M2128 |
| Penicillin-Streptomycin | SIGMA, P0781 |
| PRIME SCRIPT RT reagent kit (Perfect Real time) | Takara |
| PreMix Ex Taq | TAKARA, RR039A |
| TaqMan ® Gene Expression Assays for GAPDH Hs99999905_m1 | APPLIED BYOSISTEMS, 4331182 |
| TaqMan ® Gene Expression Assays for TNF-α Hs00174128_m1 | APPLIED BYOSISTEMS, 4331182 |
| Trypsin-EDTA solution | SIGMA, T3924 |
| α-tocopherol | SIGMA, T3251 |
| QiaExpert | Qiagen |
| 15 L digital water bath from +5° C. to +100° C. (Mod: Swbd1, BS-SWB2D) | Stuart |
| Balance (Mod. XS204) | Mettler Toledo |
| Laminar flow cabinet (Mod: Gemini) + UV lamp with anti-reflex equipment | SterilManifacturingDivision |
| HeraCell $CO_2$ incubator (Mod: 150 ADV) | ThermoScientific |
| 85° C. horizontal freezer ULT130, 120 L (Mod: Labfrost, MME-TE21140) | Elcold |
| Burker counting chamber w/clamps (DI-DA-443/3) | Carlo Erba |
| Microplateautoreader (EL 808) | Biotek |
| Vortex | Arhos160-PBI International |
| MX3000p RT instrument | Stratagene |

3.3 Biological Models Used

3.3.1 Cultures of Human Keratinocytes

The immortalized line of human keratinocytes NCTC2544 is used (Perry V. P. et al., 1957), cultured in sterile flasks (25 cm3), incubated at 37° C. in a humid atmosphere at 5% C02 in RPMI culture medium supplemented with bovine fetal serum (FBS), glutamine 2 mM in presence of 1% penicillin and streptomycin and 0.1% gentamicin. The 1:3 split is done every 2 days upon achieving the monolayer by washing with 1×PBS (phosphate buffer without $Ca^{2+}$ and $Mg^{2+}$) and detachment of cells with a trypsin-EDTA solution at 37° C. for 2 minutes. The cells were kept in culture in 25 cm3 sterile flasks and incubated at 37° C. in a humid atmosphere at 5% $CO_2$.

| ICLC CATALOG CODE | HL97002 |
| --- | --- |
| DEPOSITOR | Prof. M. Ferro, DIMES, General Pathology, University of Genoa, Italy |
| ICLC CATALOG CODE | HL97002 |
| BIBLIOGRAFIC REFERENCES | Arch Dermatol Res 1976; 256 (3): 255-260-PMID: 990102 Arch Dermatol Res 1976; 261 (1): 27-31 |

3.3.2 Controls

3.3.2.1 Induced Oxidative Stress-MTT Test

NEGATIVE CONTROL: Cells not treated in RPMI supplemented with 2.5% fetal bovine serum (FBS), glutamine 2 mM, in the presence of 1% penicillin and streptomycin and 0.1% gentamicin and kept in (96 well) culture plates at 37° C. and 5% $CO_2$ (in the dark).

POSITIVE CONTROL: Cells treated for 2 h with hydrogen peroxide 1 mM in RPMI supplemented with 2.5% fetal bovine serum (FBS), glutamine 2 mM, in presence of 1% penicillin and streptomycin and 0.1% gentamicin and kept in (96 well) culture plates at 37° C. and 5% $CO_2$ (in the dark).

3.3.2.2 Anti-Inflammatory Activity Study

NEGATIVE CONTROL: Cells not treated in RPMI supplemented with 2.5% fetal bovine serum (FBS), glutamine 2 mM, in presence of 1% penicillin and streptomycin and 0.1% gentamicin and kept in (12 well) 25 $cm^2$ culture plates at 37° C. and 5% $CO_2$.

POSITIVE CONTROL: Cells not treated in RPMI supplemented with 2.5% fetal bovine serum (FBS), glutamine 2 mM, in presence of 1% penicillin and streptomycin and 0.1% gentamicin 10 µg/mL LPS and kept in (12 well) 25 $cm^2$ culture plates at 37° C. and 5% $CO_2$.

4. Methods

4.1 Study of Protection Against Oxidative Stress Induced on Human Keratinocyte Line NCTC2544

4.2.1 Principle of the Method

Studies conducted in 2005 by Rajapakse and collaborators (2005) demonstrated the possibility to use a highly used and versatile method like that of the MTT assay to study the in vitro antioxidant activity of active compounds. Specifically, through this method it is possible to study the protective effects of such compounds on cells subsequently subjected to oxidative stress. The induction of oxidative stress is carried out by incubation with hydrogen peroxide, an agent inducing the production of oxidative damage in cells through the formation of ROS. Any protective effects can be determined through the evaluation of the cell viability post oxidative stress of cells pretreated/pre-exposed to the active compounds to be tested, compared to cells subjected to the same oxidative stress. A higher cell viability will correspond to a protective effect of the compounds tested.

4.2.2 Experimental Procedure

The assay was conducted in accordance with the method described by Coda and collaborators (Coda et al., 2012), with some changes.

Human keratinocytes NCTC2544 were seeded in a 96-well plate at the density of $5*10^4$ cells/well and incubated at 37° C. at 5% $CO_2$ until reaching about 80% confluence.

Then, the cells were incubated for 16 hours with the active compounds to be tested and the respective controls at the following concentrations: 100-250 and 500 µg/mL respectively for samples B, FER867, FER868, FER869, FER870 and FER871.

The dilutions were prepared starting from stock 50 mg/mL in DMSO, sterile-filtered and using RPMI medium supplemented at 2.5% fetal bovine serum (FBS), glutamine 2 mM, in presence of 1% penicillin and streptomycin and 0.1% gentamicin. Cells treated with $H_2O_2$ 1 mM were used as a positive control; cells kept in culture medium alone (RPMI 2.5% FBS) were used instead as a negative control.

Alpha tocopherol was tested as a reference antioxidant at the concentration of 100, 250 and 500 µg/mL respectively.

After 16 hours of pretreatment, the cells were washed with PBS 1× and incubated for 90 minutes with a 1 mm $H_2O_2$ solution (Sigma-Aldrich, St. Louis, Mo., USA) in serum-free medium, in the dark, at 37° C. and 5% $CO_2$.

Once the oxidative stress induction step was concluded, the cell viability of the various samples was evaluated according to the method described in point 4.1.2 (MTT assay).

The data were expressed as percentage of cell viability compared with control cells (ctr) not stressed, according to the following formula:

% cell viability/ctr=(Abs sample/Absctr)*100

All the assays were performed at least two times in duplicate.

4.3 Study of Anti-Inflammatory Activity (TNF-α)

4.4.1 Experimental Procedure

The gene expression of the TNF-α inflammation marker in NCTC2544 cells was evaluated by relative quantitative RT-PCR (quantitative reverse transcription-polymerase chain reaction-qRT-PCR).

This analysis required 3 sequential steps:
extraction of total RNA;
retrotranscription in cDNA;
qRT-PCR.

Human keratinocytes NCTC2544 were seeded in 12-well plates at the density of $0.5*10^6$ cells/well and incubated until reaching about 80% confluence.

Then, the cells were incubated for 16 and 24 hours respectively with samples B, FER867, FER868, FER869, FER870 and FER871 at the following concentrations: 100, 250 and 500 µg/mL.

The dilutions were prepared starting from stock 50 mg/mL in culture medium (RPMI), supplemented at 2.5% fetal bovine serum (FBS), glutamine 2 mM, in presence of 1% penicillin and streptomycin and 0.1% gentamicin.

LPS (Lipopolysaccharide) was used in an amount of 10 µg/mL as inducer of inflammation and co-incubated with treatment solutions for 16 and 24 h.

Cells kept in the culture medium alone (RPMI 2.5% FBS) were used as a negative control.

Cells kept in the culture medium alone (RPMI 2.5% FBS) and 10 µg/mL LPS were instead used as a negative control.

After incubation, the RNA was extracted.

Total RNA was extracted from NCTC2544 cells according to what was described by Chomczynski and Mackey (1995).

After the incubation with the active compounds of interest, cells were washed with PBS (1×) and finally subjected to RNA extraction procedure. After the extraction, the extracted RNA was quantified using the QiaExpert (Qiagen) instrument and the concentrations in µg/mL of total RNA extracted at the 260 nm wavelength were calculated.

Finally, the integrity of RNA (2 µg/mL) was evaluated by means of an electrophoresis run on 1% agarose gel.

The total RNA was converted into cDNA (complementary DNA), using an enzyme capable of synthesizing a DNA molecule using a strand of RNA as a template; this DNA-polymerase RNA-dependent enzyme is called reverse transcriptase.

It binds to the 3' end of a single strand of RNA and through random primers and deoxynucleoside triphosphate (DNTPS) it synthesizes the strand of cDNA.

For this purpose, a commercial kit "PrimeScript™ RT Reagent Kit (perfect Real Time)" (TakaraBioInc., Japan) was used, containing 5× PrimeScript Buffer (for real Time); PrimeScript RT Enzyme Mix1; OligodTPrimer; Random 6 mers; RNAse free 2 $dH_2O$.

The extracted and quantified RNA was diluted to a concentration of 2 µg/mL and reverse transcribed into cDNA. A Master Mix of 10 µL (containing 5× PrimeScript Buffer (for real Time); PrimeScript RT Enzyme Mix1; OligodTPrimer 50 µPM; Random 6 mers 100 µM) was prepared, to which 10 µL of RNA (2 µg/mL) were added.

The samples were placed in a thermal cycler (Stratagene Mx3000P Real Time PCR System, Agilent Technologies Italy S.p.A., Milan, Italy) and subjected to retrotranscription under the following conditions:
37° C. for 15 minutes;
85° C. for 5 seconds;
4° C. hold.

After the retrotranscription, to the samples 30 µL of DEPC water were added to obtain a final concentration of cDNA of 40 ng/µL.

The qRT-PCR is a real-time amplification and quantification method of amplified products by monitoring the fluorescence emitted during the reaction.

For RT-PCR amplification, the TaqMan® (AppliedBiosystems) probe system was used. The following TaqMan probes were used: Hs00174128_m1 (TNF-α) and Hs99999905_m1 (GAPDH). GAPDH. Hs99999905_m1 was used as control gene (housekeeping).

The Taqman probe is a type of probe that allows the development of fluorescence as the amplification advances. A reporter (fluorophore FAM™) is bound to its 5' end while a quencher is bound to the 3' end. The closeness between the reporter and the quencher cancels the fluorescence signal emission. Only with the 5' esonucleasic activity of thermostable DNA polymerase (Taq polymerase) fluorescence is detected and the accumulation of the amplification products can be evaluated through the increase of fluorescence of the reporter which increases during each cycle.

A Master Mix was set up for the qRT-PCR as follows:
10 µL of "2× Premix Ex Taq";
1 µL of "20× TaqMan Gene Expression Assays" (containing 2 primers and the fluorophore-labelled fluorescent probe FAM™);
0.4 µL of passive reference Rox II;
5 µL of DEPC water.
4 µL of cDNA were added to the Master Mix for the target gene and 1 PL of cDNA for the housekeeping gene.

The amplification was carried out for 40 runs under the following conditions:
95° C., 30 sec (Amplitaqactivation);
95° C., 5 sec (Denaturation)
60° C., 20 sec (Annealing—extension);
Each analysis was conducted in duplicate.

The data obtained were analysed according to the method of $2^{-\Delta\Delta Ct}$ and therefore it was possible to calculate the relative values of expression of the gene of interest, normalized compared to the housekeeping gene and calibrated on the control sample (untreated cells):

$$\Delta\Delta Ct = \Delta Ct_{target\text{-}housekeeping}(\text{control}) - \Delta Ct_{target\text{-}housekeeping}(\text{treated cells})$$

The $2^{-\Delta\Delta Ct}$ was calculated assuming an amplification efficiency of 100%.

5. Results

5.1 Protection Assay Against Induced Oxidative Stress

Figure 5:
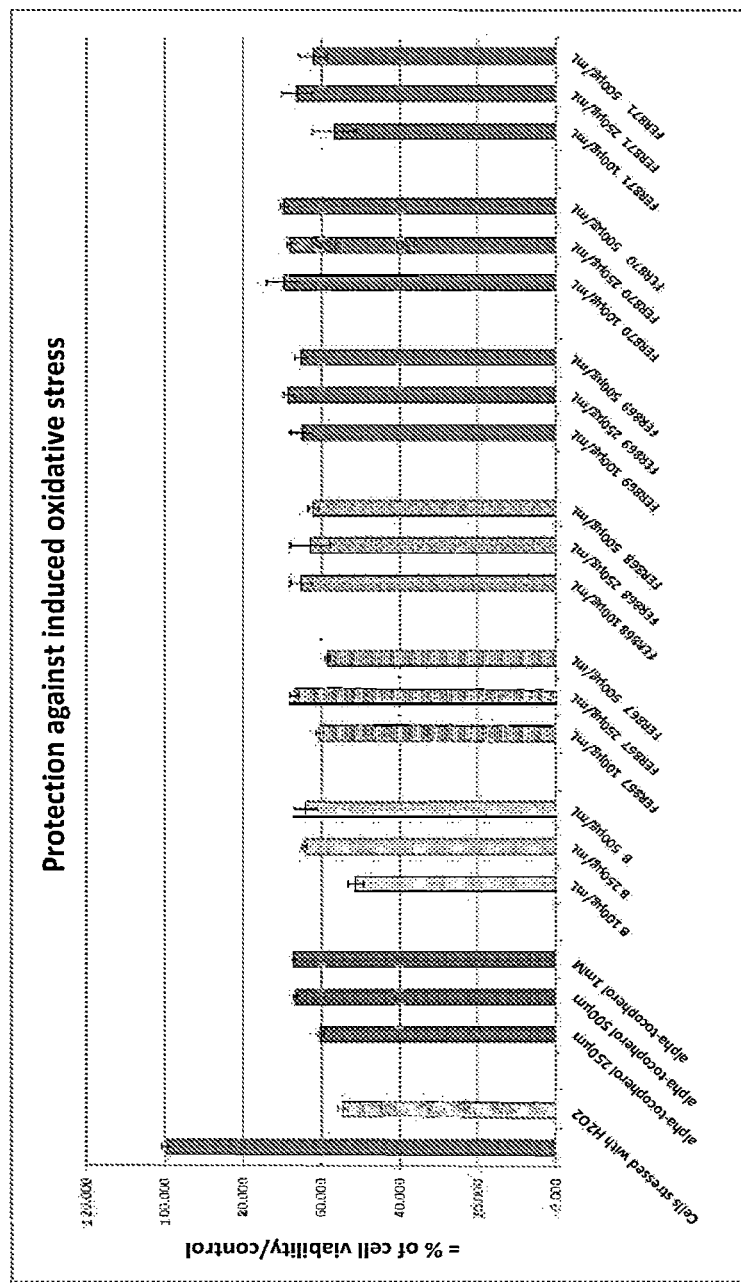
FIG. 5 shows bar graphs related to the percentage of cell viability on human keratinocytes NCTC2544 following induction of oxidative stress induced with $H_2O_2$ 1 mM according to the test of Example 12. The cells were previously incubated for 16 h with 100, 250 and 500 μg/ml of sample B, FER867, FER868, FER869, FER870 and FER871. Untreated cells (Control). Cells treated with $H_2O_2$ 1 mM (Cells stressed with H2O2). * ($p<0.05$),  ($p<0.01$), * ($p<0.005$), **** ($p<0.001$).

FIG. 5 shows the data related to the activity of protection against induced oxidative stress of the samples tested in comparison with an antioxidant of known action, α-tocopherol.

The results show a significant protection activity against induced oxidative stress for all the compounds analysed at concentrations of 250 and 500 μg/mL and this activity is comparable to that of α-tocopherol.

5.2 Study of Anti-Inflammatory Activity (TNF-α)

The enclosed FIGS. 6 A and B show the TNF-α gene expression data, respectively after 16 h (FIG. 6a) and 24 h (FIG. 6B) treatment with the samples: sample B (CONTROL), FER867, FER868, FER869, FER870 and FER871, respectively at concentrations of 100-250 and 500 μg/mL.

After 16 hours of treatment, samples B, and FER867 tested at concentrations of 100, 250 and 500 μg/mL show the most significant anti-inflammatory activity (FIG. 6A).

The anti-inflammatory activity is more evident after 24 hours of treatment (FIG. 6B), in particular for the FER867 sample.

6. Conclusions

In conclusion, the tests carried out showed a significant protection activity against the induced oxidative stress for all the samples tested at concentrations of 250 and 500 μg/mL (FIG. 5).

Furthermore, the study of anti-inflammatory activity showed that after 16 hours of treatment, samples B, FER867 tested at concentrations of 100 and 250 μg/mL show a significant anti-inflammatory activity (FIG. 6A).

For compound FER869, the concentration of 500 μg/ml significantly reduced the TNF-alpha-associated mRNA expression. FER871 at concentrations of 100 and 500 μg/mL shows a reduction in mRNA production. The anti-inflammatory activity of tested compounds is more evident after 24 hours of treatment (FIG. 6B), in particular for the FER867 compound.

BIBLIOGRAPHY

Arch Dermatol Res 1976; 256 (3): 255-260-PMID: 990102

Arch Dermatol Res 1976; 261 (1): 27-31

Mosmann T, 1983. Rapid Colorimetric Assay for Cellular Growth and Survival: Application to Proliferation and Cytotoxicity Assays. J Immunol Methods 65(1-2), 55-63.

Rajapakse N, Mendis E, Byun H G, Kim S K, 2005. Purification and in vitro antioxidative effects of giant squid muscle peptides on free radical-mediated oxidative systems. J NutrBiochem 16(9), 562-569.

Coda R, Rizzello C G, Pinto D, Gobbetti M, 2012. Selected Lactic Acid Bacteria Synthesize Antioxidant Peptides during Sourdough Fermentation of Cereal Flours. Appl Environ Microbiol 78(4), 1087-1096.

Chomczynski P, Mackey K. Modification of the TRI reagent procedure for isolation of RNA from polysaccharide- and proteoglycan-rich sources. Biotechniques 1995; 19:942-5.

Example 13

Soft Jelly Capsule
  Each soft jelly capsule (pearl) contains: . . . q.ty u.m.
  Pollen fermented with selected *Lactobacillus kunkeei* strains PF12, PF15 and PL13 without the yeast inoculation ref. Example 5 . . . 100 mg
  Soybean oil . . . 250 mg
  Soy lecithin . . . 5 mg
  Mono and di-glycerides of fatty acids . . . 30 mg
Constituents of the Shell:
  Gelatin . . . 145 mg
  Glycerol . . . 67 mg

Example 14

Tablet
  Each dose contains . . . q.ty u.m.
  Pollen fermented with selected *Lactobacillus kunkeei* strains PF12, PF15 and PL13 without the yeast inoculation ref. Example 5 . . . 200 mg
  Microcrystalline cellulose . . . 100 mg
  BioGABA [gamma-aminobutyric acid from fermentation of grape must (*Vitis vinifera* L. fruits), *Lactobacillus plantarum* C48] . . . 100 mg
  Polyvinylprorrolidone . . . 35 mg
  Rice (*Oryza sativa* L. seed dry extract) . . . 50 mg
  Alfalfa (*Medicago sativa* L. flower dry extract . . . 40 mg
  Chlorella (*Chlorella pyrenoidosa* H. Chick) thallus dry extract . . . 30 mg
  Phosphatidylserine . . . 40 mg
  Melissa (*Melissa officinalis* L.) leaves and flowers dry extract 100 mg
  Griffonia [*Griffonia simplicifolia* (DC.) Baill] seeds dry extract . . . 51 mg
  L-Theanine . . . 12.6 mg
  Silicon dioxide . . . 10 mg
  Magnesium stearate . . . 10 mg

Example 15

Chewable Tablets
  Each dose contains . . . q.ty u.m.
  Maltodextrin . . . 50-300 mg
  Dextrose . . . 50-300 mg
  Fructose . . . 50-300 mg
  Pollen fermented with the selected strains *Lactobacillus kunkeei* PF12, PF15 and PL13 without inoculation of yeast ref. Example 5 . . . 100 mg
  Aroma . . . 10-30 mg
  Corn starch . . . 10-30 mg
  Microcrystalline cellulose . . . 10-30 mg
  Silicon dioxide . . . 5-15 mg
  Leucine . . . 5-15 mg

Example 16

Tablets
  Each dose contains . . . q.ty u.m.
  Calcium phosphate . . . 150 mg
  Pollen fermented with selected *Lactobacillus kunkeei* strains PF12, PF15 and PL13 without the yeast inoculation ref. Example 5 . . . 50 mg
  Boswellia (*Boswellia serrrata* Roxb.) Dry extract resin . . . 150 mg
  Palmitoylethanolamide (PEA) . . . 150 mg BioGABA [gamma-aminobutyric acid from grape must fermentation (*Vitis vinifera* L. fruits) *Lactobacillus plantarum* C48] . . . 100 mg
Gamma aminobutyric acid . . . 49 mg
Turmeric (*Curcuma longa* L.) rhizome dry extract . . . 100 mg
Microcrystalline cellulose . . . 50 mg
Vitamin D (Colecalciferol) . . . 0.005 mg
Vitamin B3 (Nicotinamide) . . . 16 mg
Hydroxy-propyl cellulose . . . 30 mg
Silicon dioxide . . . 6 mg
Mono and diglycerides of fatty acids . . . 10 mg
Vitamin B1 (Thiamine mononitrate) . . . 1.36 mg
Vitamin B2 (Riboflavin) . . . 1.4 mg
Vitamin B5 (Calcium Pantothenate) . . . 6.5 mg
Vitamin B6 (Pyridoxine hydrochloride) . . . 1.7 mg
Vitamin K2 (Menaquinone-7) 0.075 mg
Vit B12 (Cyanocobalamin) . . . 0.026 mg

Example 17

Tablets
Each dose contains . . . q.ty u.m.
Ashwagandha (*Withania somnifera* L. Dunal) root dry extract . . . 150 mg
Pollen fermented using the mixed starter composed of the selected strains *Lactobacillus kunkeei* PF12, PF15 and PL13 and of the yeast *Hanseniaspora uvarum* AN8Y27B ref. Example 4 . . . 50 mg
Microcrystalline cellulose . . . 100 mg
Magnesium oxide . . . 100 mg
*Bacopa* (*Bacopa monnieri* L. Pennel) dry extract top . . . 100 mg
BioGABA [gamma-aminobutyric acid from fermentation of grape must (*Vitis vinifera* L. fruit), *Lactobacillus plantarum* C48] . . . 100 mg
Calcium phosphate . . . 100 mg
Gamma-aminobutyric acid . . . 49 mg
Saffron (*Crocus sativus* L.) flower extract . . . 30 mg
Hydroxypropyl methylcellulose . . . 30 mg
Zinc bisglycinate . . . 10 mg
Silicon dioxide . . . 7 mg
(6S)-5-methyltetrahydrofolic acid, glucosamine salt . . . 0.2 mg
Magnesium stearate . . . 11 mg

Example 18

Immunostimulant Bar 30 Grams
Pollen fermented with the selected strains *Lactobacillus kunkeei* PF12, PF15 and PL13 without inoculation of yeast ref. Example 5 . . . 2 g
Glucose and fructose syrup . . . 10-14 g
Rice flakes . . . 10-12 g
Sunflower lecithin . . . 0.5-3 g
Palm oil (*Elaeis guinensis*) . . . 0.5-3%
Corn maltodextrin . . . 1-2 g
Acai (*Euterpe oleracea*) dehydrated fruit . . . 3-4 g
Raisins (*Vitis apyrena* L.) dehydrated fruit . . . 1-2 g
Citric acid . . . q.b
Aroma . . . q.b

Example 19

Hard Jelly Capsules
Each hard jelly capsule contains: . . . q.ty u.m.
Pollen fermented using the mixed starter composed of the selected strains *Lactobacillus kunkeei* PF12, PF15 and PL13 and of the yeast *Hanseniaspora uvarum* AN8Y27B ref. Example 4 . . . 200 mg
Maltodextrin . . . 5-50 mg
Insoluble natural fiber . . . 5-100 mg
Magnesium stearate . . . 1-10 mg
Silicon dioxide . . . 3-6 mg
Natural jelly outer envelope . . .

Example 20

Oral Soluble Granulate
Each sachet contains: . . . q.ty u.m.
Pollen fermented using the mixed starter composed of the selected strains *Lactobacillus kunkeei* PF12, PF15 and PL13 and of the yeast *Hanseniaspora uvarum* AN8Y27B ref. Example 4 . . . 1000 mg
Inulin . . . 200-600 mg
Maltodextrin . . . 0.5-3.0 g
Malic acid . . . 1-10 mg
Aroma . . . 10.0-50.0 mg
Sucralose . . . 0.005 mg

Example 21

Granular Blend in Stick Pack
Each sachet contains: . . . q.ty u.m.
Pollen fermented with the selected strains *Lactobacillus kunkeei* PF12, PF15 and PL13 without inoculation of yeast ref. Example . . . 5 500 mg
Echinacea (*Echinacea purpurea*) aerial parts dry extract . . . 300 mg
Honey aroma . . . 10 mg
Inulin . . . 1-2 g
Arabic gum . . . 0.5-2 g
Malic acid . . . 0-100 mg
Sucralose . . . 0.005 mg
Aroma . . . 0.25 mg

Example 22

Tablet
Each tablet contains:
Pollen fermented with the selected strains *Lactobacillus kunkeei* PF12, PF15 and PL13 without inoculation of yeast ref. Example . . . 5 50 mg
Microcrystalline cellulose . . . 50 mg
Broccoli (*Brassica oleracea italica* var.) inflorescence dry extract . . . 125 mg
BioGABA [gamma-aminobutyric acid from fermentation of grape must (*Vitis vinifera* L. fruits) . . . 100 mg
Fermented pollen . . . 100 mg
Mustard (*Brassica juncea* L. Czern.) seed dry extract . . . 75 mg
Artichoke (*Cynara scolymus* L.) leaves dry extract . . . 60 mg
Acerola (*Malpighia glabra* L.) fruit dry extract . . . 100 mg
Orange (*Citrus sinensis* L.) fruit dry extract . . . 50 mg
Calcium phosphate . . . 50 mg
Beetroot (*Beta vulgaris* L.) whole plant dry extract . . . 50 mg Hydroxypropyl cellulose . . . 20 mg
Bayberry (*Myrica cerifera* L.) bark dry extract . . . 30 mg
*Astragalus* (*Astragalus membranaceus*) root dry extract . . . 30 mg
Quercetin . . . 30 mg
Vitamin E (Tocotrienol tocopherol) . . . 6 mg
Beta-sitosterol . . . 20 mg
Lycopene . . . 10 mg
Nicotinamide . . . 16 mg
Silicon dioxide . . . 10 mg
Mono and diglycerides of fatty acids . . . 10 mg
*Galeopsis* (*Galeopsis segetum* Necker) aerial parts dry extract 5 mg
Spermidine trichlorohydrate . . . 0.5 mg
Biotin . . . 0.05 mg

The invention claimed is:

1. A microbiological process for a production of bee bread-like fermented pollen comprising a step a) of inoculation of pollen in grains with a starter lactic acid bacterium and a step b) of fermentation of the pollen, wherein the inoculated starter lactic acid bacterium is a mixture of *Lactobacillus kunkeei* strains selected from *Lactobacillus kunkeei* PF12 having the accession number DSM 32843, *Lactobacillus kunkeei* PF15 having the accession number DSM 32845, and *Lactobacillus kunkeei* PF13 having the accession number DSM 32844.

2. The process according to claim 1, comprising a preliminary treatment of the pollen grains for degrading an outer coating layer and making a grain content available for a fermentative activity of the inoculated starter lactic acid bacterium inoculated in step a).

3. The process according to claim 1, comprising an inoculation of a yeast which degrades or metabolizes a coating pectinic component of the pollen in grains, in a step before step a) or in a step a).

4. The process according to claim 3, wherein said yeast which degrades or metabolizes the coating pectinic component of the pollen in grain belongs to *Wickerhamomyces anomalus* or *Hanseniaspora uvarum*.

5. The process according to claim 1, comprising a further step c) of abatement of microbial charge after the fermentation step.

6. The process according to claim 1, comprising a further step of drying.

7. The process according to claim 6, wherein the step of drying is freeze drying or spray drying.

* * * * *